(12) United States Patent
Rotunda et al.

(10) Patent No.: US 11,986,443 B2
(45) Date of Patent: *May 21, 2024

(54) ALCOHOL-BASED COMPOSITIONS AND USES THEREOF

(71) Applicant: Polithera, Inc., Newport Beach, CA (US)

(72) Inventors: Adam M. Rotunda, Newport Beach, CA (US); Vince Afsahi, Newport Beach, CA (US)

(73) Assignee: Polithera, Inc., Newport Beach, CA (US)

( * ) Notice: Subject to any disclaimer, the term of this patent is extended or adjusted under 35 U.S.C. 154(b) by 229 days.

This patent is subject to a terminal disclaimer.

(21) Appl. No.: 17/488,041

(22) Filed: Sep. 28, 2021

(65) Prior Publication Data

US 2022/0016050 A1 Jan. 20, 2022

Related U.S. Application Data

(63) Continuation-in-part of application No. 17/030,252, filed on Sep. 23, 2020, which is a continuation-in-part of application No. 16/653,617, filed on Oct. 15, 2019, now Pat. No. 10,835,502.

(60) Provisional application No. 63/089,843, filed on Oct. 9, 2020, provisional application No. 62/904,526, filed on Sep. 23, 2019, provisional application No. 62/752,404, filed on Oct. 30, 2018, provisional application No. 62/746,447, filed on Oct. 16, 2018.

(51) Int. Cl.
| | | |
|---|---|---|
| *A61K 31/08* | (2006.01) | |
| *A61K 9/00* | (2006.01) | |
| *A61K 31/045* | (2006.01) | |
| *A61K 45/06* | (2006.01) | |
| *A61P 43/00* | (2006.01) | |

(52) U.S. Cl.
CPC ............ *A61K 31/08* (2013.01); *A61K 9/0019* (2013.01); *A61K 31/045* (2013.01); *A61K 45/06* (2013.01); *A61P 43/00* (2018.01)

(58) Field of Classification Search
CPC .... A61K 31/08; A61K 9/0019; A61K 31/045; A61K 45/06; A61P 43/00
USPC ......................................................... 514/723
See application file for complete search history.

(56) References Cited

U.S. PATENT DOCUMENTS 9,351,945 B1 * 5/2016 Dobak, III ............. A61K 31/08
10,835,502 B2 * 11/2020 Rotunda ................. A61P 35/00

* cited by examiner

*Primary Examiner* — Yevgeny Valenrod
(74) *Attorney, Agent, or Firm* — STETINA BRUNDA GARRED & BRUNDA

(57) ABSTRACT

This disclosure relates to a method of reducing a fat deposit comprising injecting an alcohol-containing pharmaceutical composition into the fat deposit. The method may be effective in improving the appearance of or reducing the weight or volume of the fat deposit.

20 Claims, 21 Drawing Sheets

Pre-injection 5.5 x 4.5 cm

Mobile, Firm 2 wks after 1st injection 5 x 3.5 cm

Flattening 3 wks after 2<sup>nd</sup> injection 5 x 3.5 cm

Flattening and nodular

Right Elbow Lipoma, 59 Year-Old Woman

Before 1.8 x 0.4 x 1.8 (1.3 cm³)

Right Elbow Lipoma, 59 Year-Old Woman

After 1.6 x 0.5 x 1.1 cm (0.9 cm$^3$)

Right Forearm Lipoma, 59 YO Woman

Before 2.1 x 0.9 x 1.8 cm (3.4 cm³)

Right Forearm Lipoma, 59 YO Woman

After 1.4 x 0.6 x 1.4 cm (1.2 cm$^3$)

Right upper back lipoma, 4 x 2 cm soft skin mass, adjacent to scar

Same lipoma, 6 weeks after 2 treatments (total of 5 mL 1% polidocanol + EtOH)

2 x 2 cm soft, and now flatter skin mass

Right Upper Back Lipoma, 78 YO Man

Before 4 x 2.3 x 0.9 cm (8.3 cm³)

Right Upper Back Lipoma, 78 YO Man

Right Upper Back Lipoma, 78 YO Man

After 2.1 x 1.7 x 0.9 cm (3.2 cm³)

FIG. 7 Normal fat (4x and 10x, H&E)

ALCOHOL-BASED COMPOSITIONS AND USES THEREOF

CROSS-REFERENCE TO RELATED APPLICATIONS

This application claims the benefit of U.S. Provisional Patent Application No. 63/089,843, filed Oct. 9, 2020; this application is a continuation-in-part of U.S. patent application Ser. No. 17/030,252, filed Sep. 23, 2020, which is a continuation-in-part of U.S. patent application Ser. No. 16/653,617, filed Oct. 15, 2019, now U.S. Pat. No. 10,835,502; which claims the benefit of U.S. Provisional Application Nos. 62/746,447, filed Oct. 16, 2018, 62/752,404, filed Oct. 30, 2018, and 62/904,526, filed Sep. 23, 2019; all of which are incorporated by reference herein in their entireties.

BACKGROUND

There continues to be a need for injectable products for the reduction of fat deposits in various areas of an animal or a human body.

SUMMARY

Some embodiments include a method of reducing a fat deposit comprising injecting a pharmaceutical composition into the fat deposit, wherein the pharmaceutical composition comprises an alcohol, wherein the method is effective in improving the appearance of the fat deposit, and/or reducing the weight or volume of the fat deposit.

Some embodiments include use of a pharmaceutical composition comprising an alcohol described herein in the manufacture of a medicament for reducing a fat deposit.

Some embodiments include a pharmaceutical composition comprising an alcohol described herein for reducing a fat deposit.

Some embodiments include a kit comprising a pharmaceutical composition and written instructions directing that the composition be injected into a fat deposit, wherein the pharmaceutical composition comprises an alcohol, wherein the method is effective in reducing the weight or volume of the fat deposit.

DETAILED DESCRIPTION

Figure 1A:
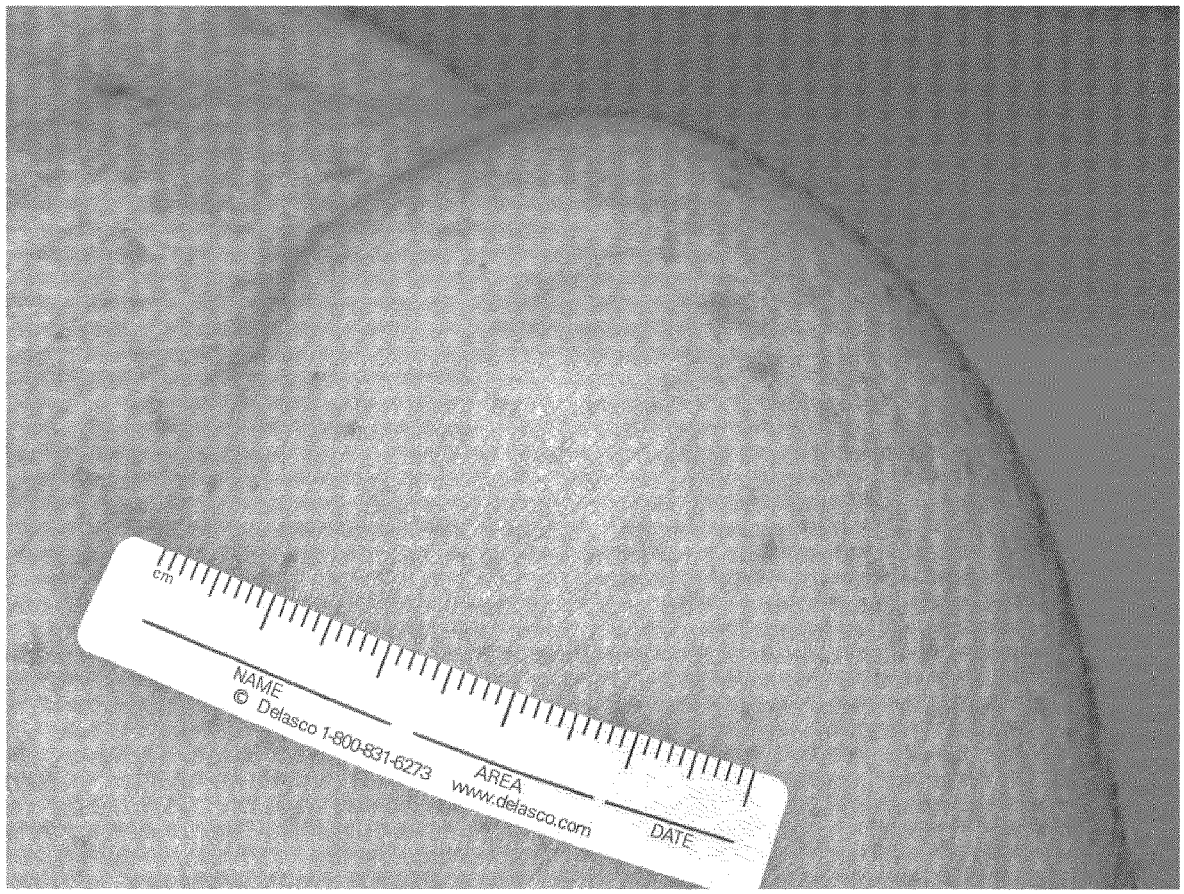
FIG. 1A is a photograph of the left shoulder of Patient 6 before injection.
Figure 1B:
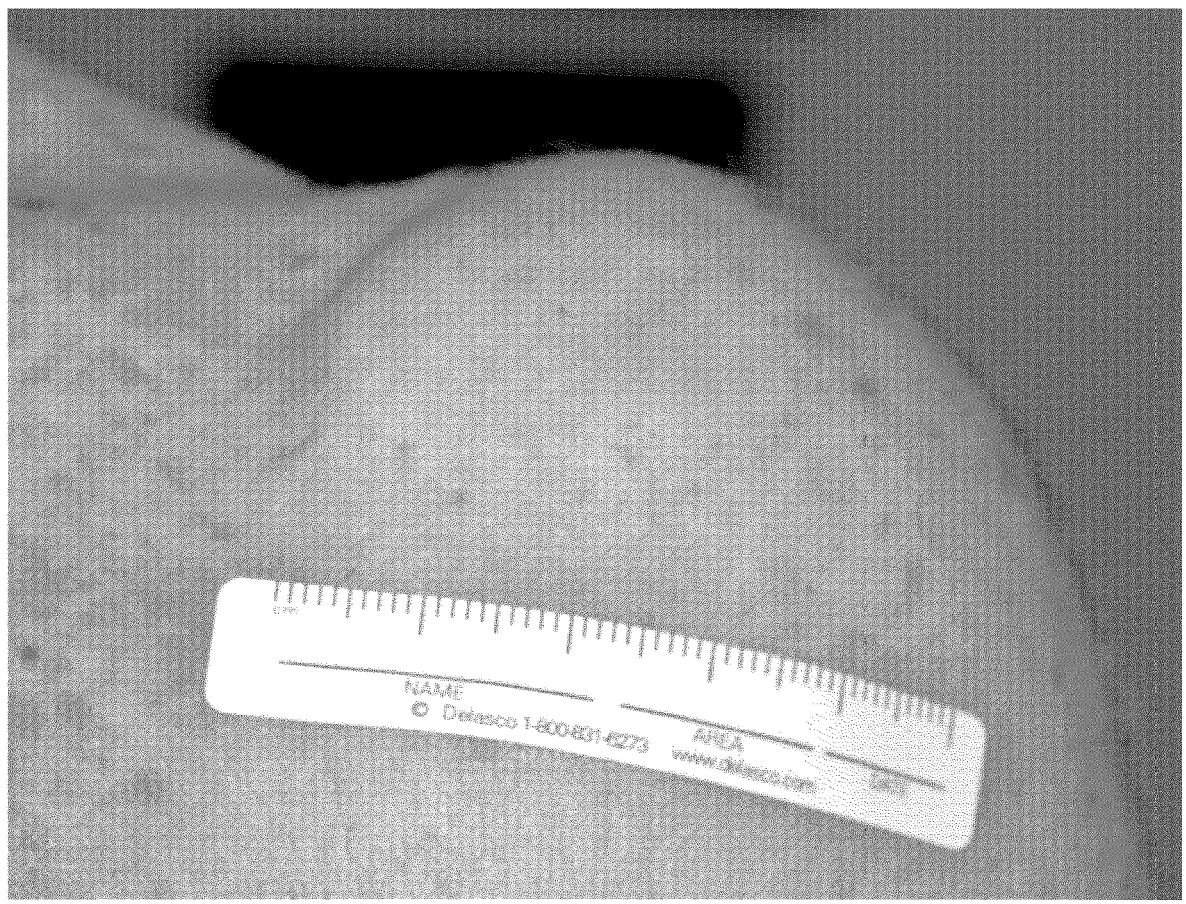
FIG. 1B is a photograph of the left shoulder of Patient 6 two weeks after her first injection as described in Example 3.
Figure 1C:
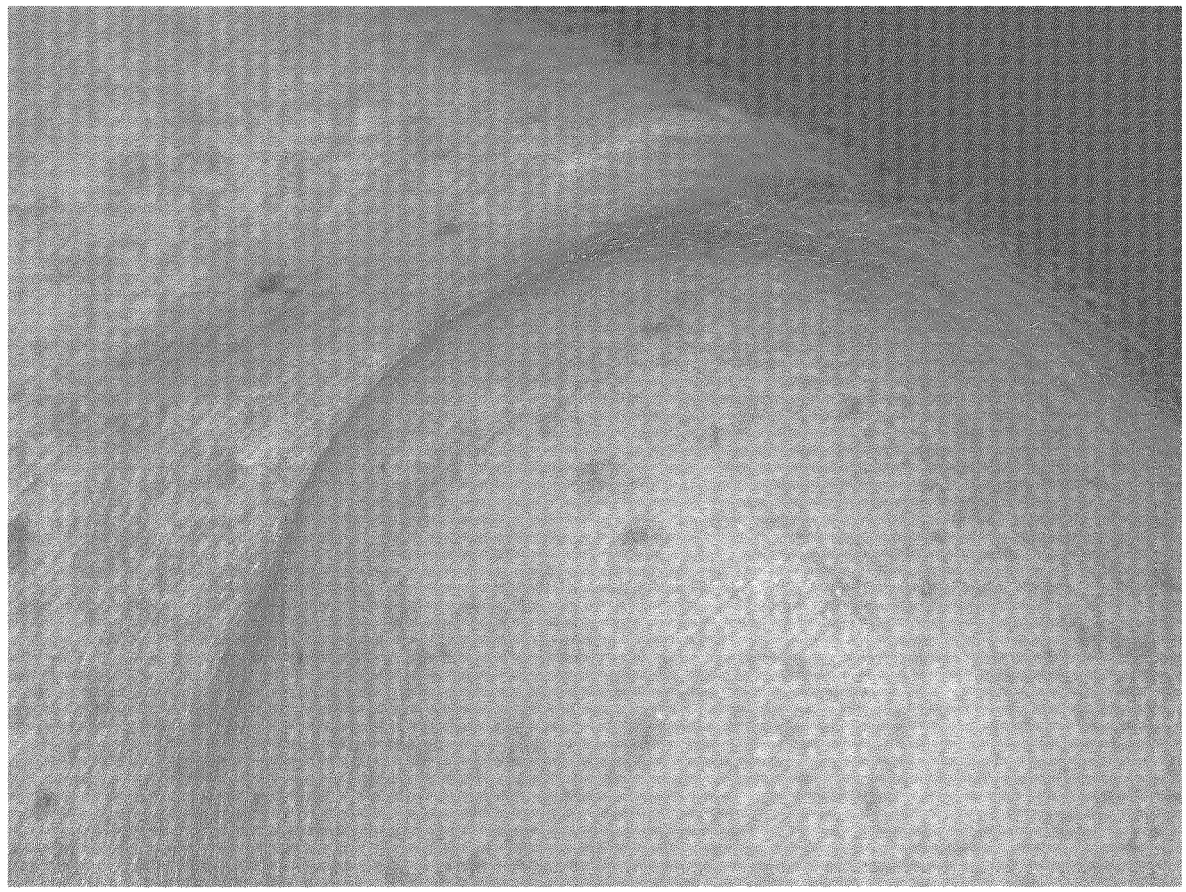
FIG. 1C is a photograph of the left shoulder of Patient 6 three weeks after her first injection as described in Example 3.
Figure 2A:
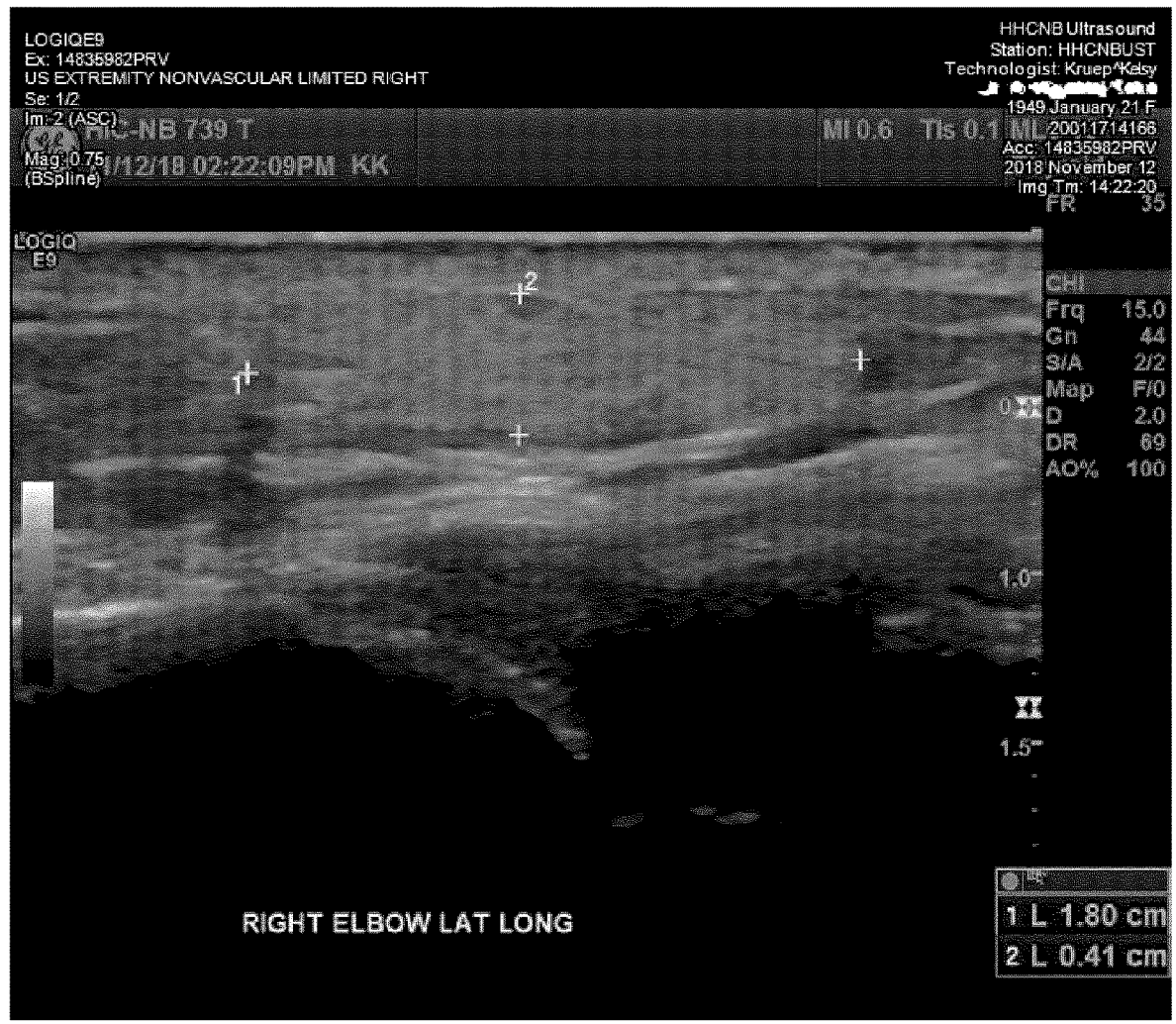
FIG. 2A is an ultrasound of the right elbow of Patient 2 before injection.
Figure 2B:
FIG. 2B is an ultrasound of the right elbow of Patient 2 after injection as described in Example 3.
Figure 3A:
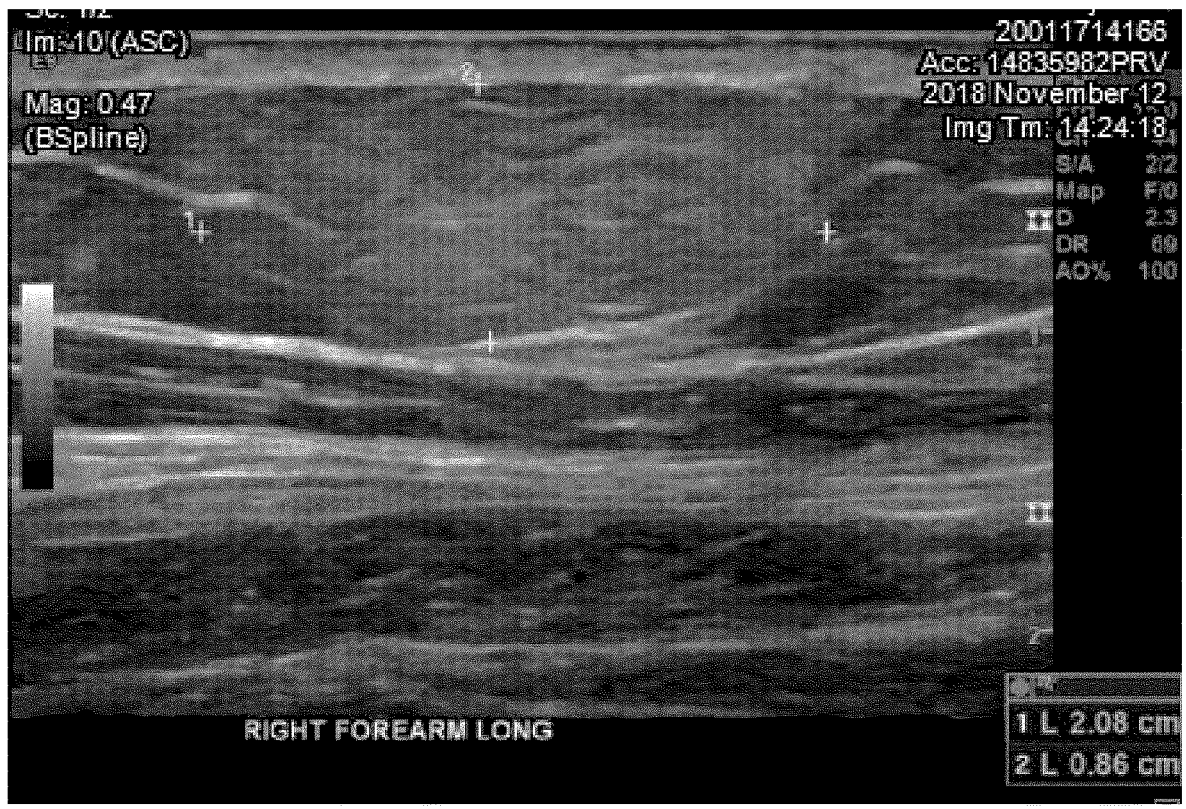
FIG. 3A is an ultrasound of the right forearm of Patient 2 before injection.
Figure 3B:
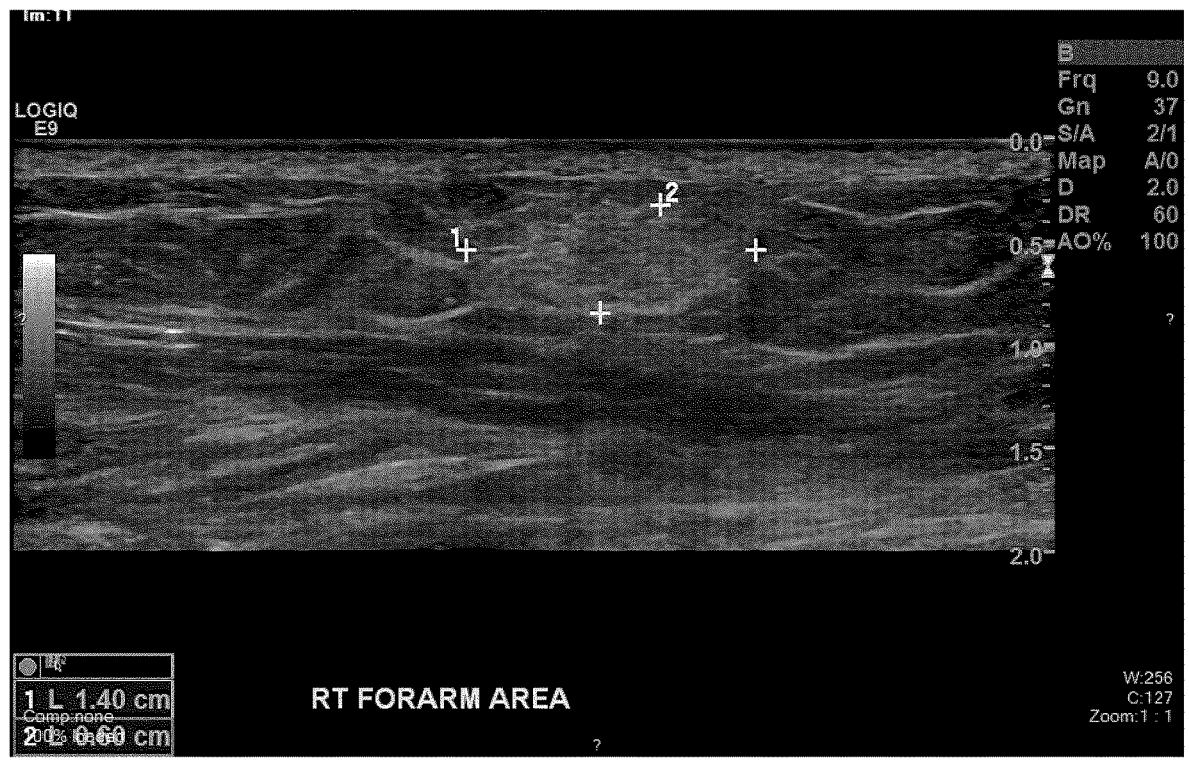
FIG. 3B is an ultrasound of the right forearm of Patient 2 after injection as described in Example 3.
Figure 4A:
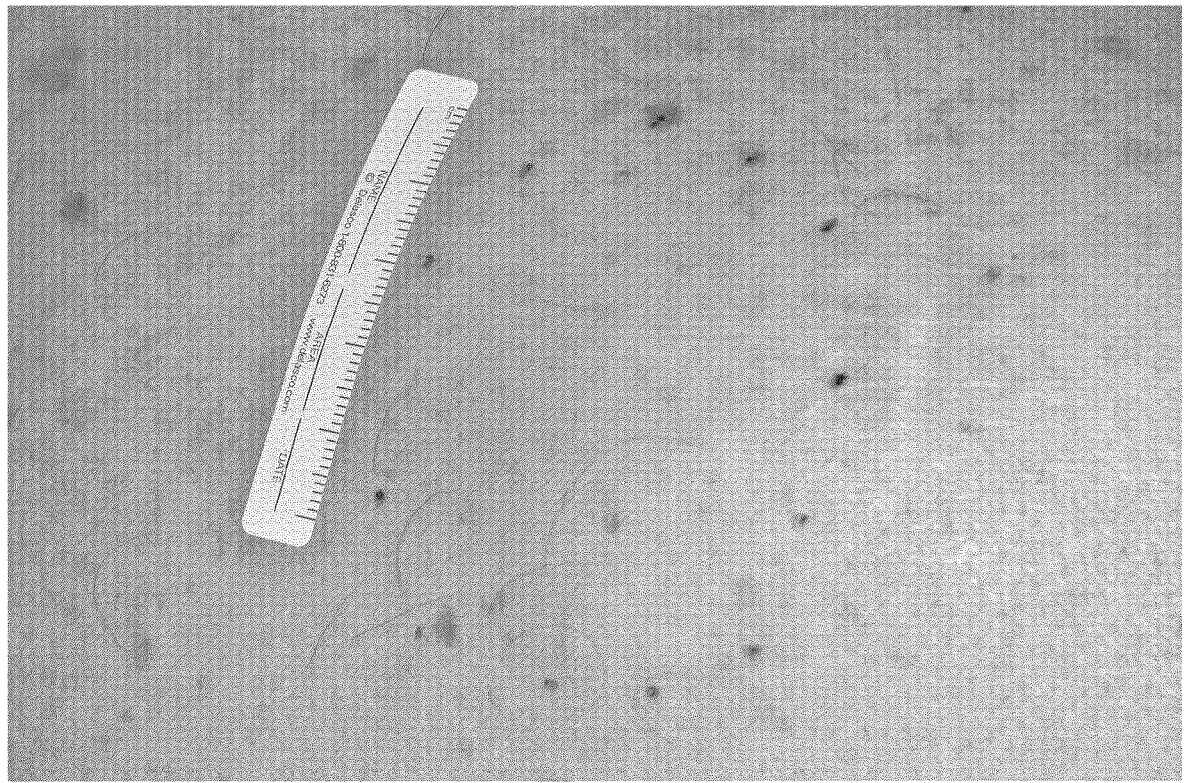
FIG. 4A is a photograph of the right upper back of Patient 4 before injection.
Figure 4B:
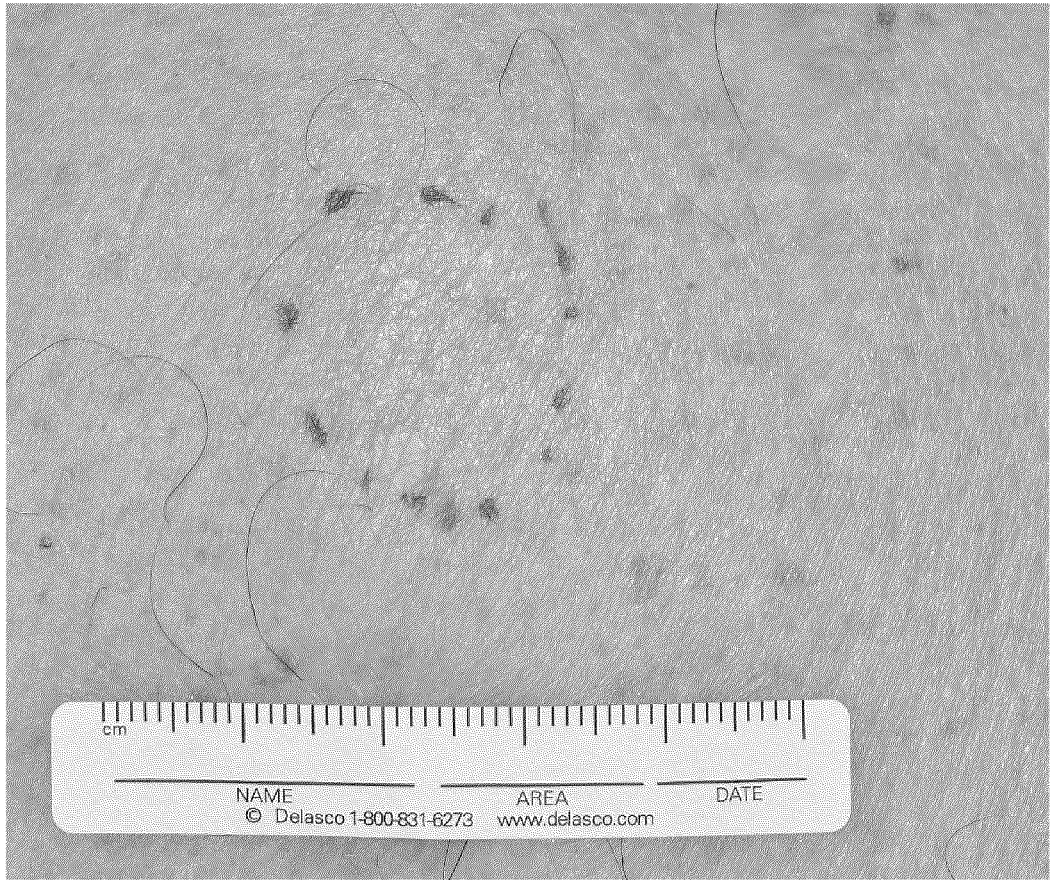
FIG. 4B is a photograph of the right upper back of Patient 6 weeks after two treatments as described in Example 3.
Figure 5A:
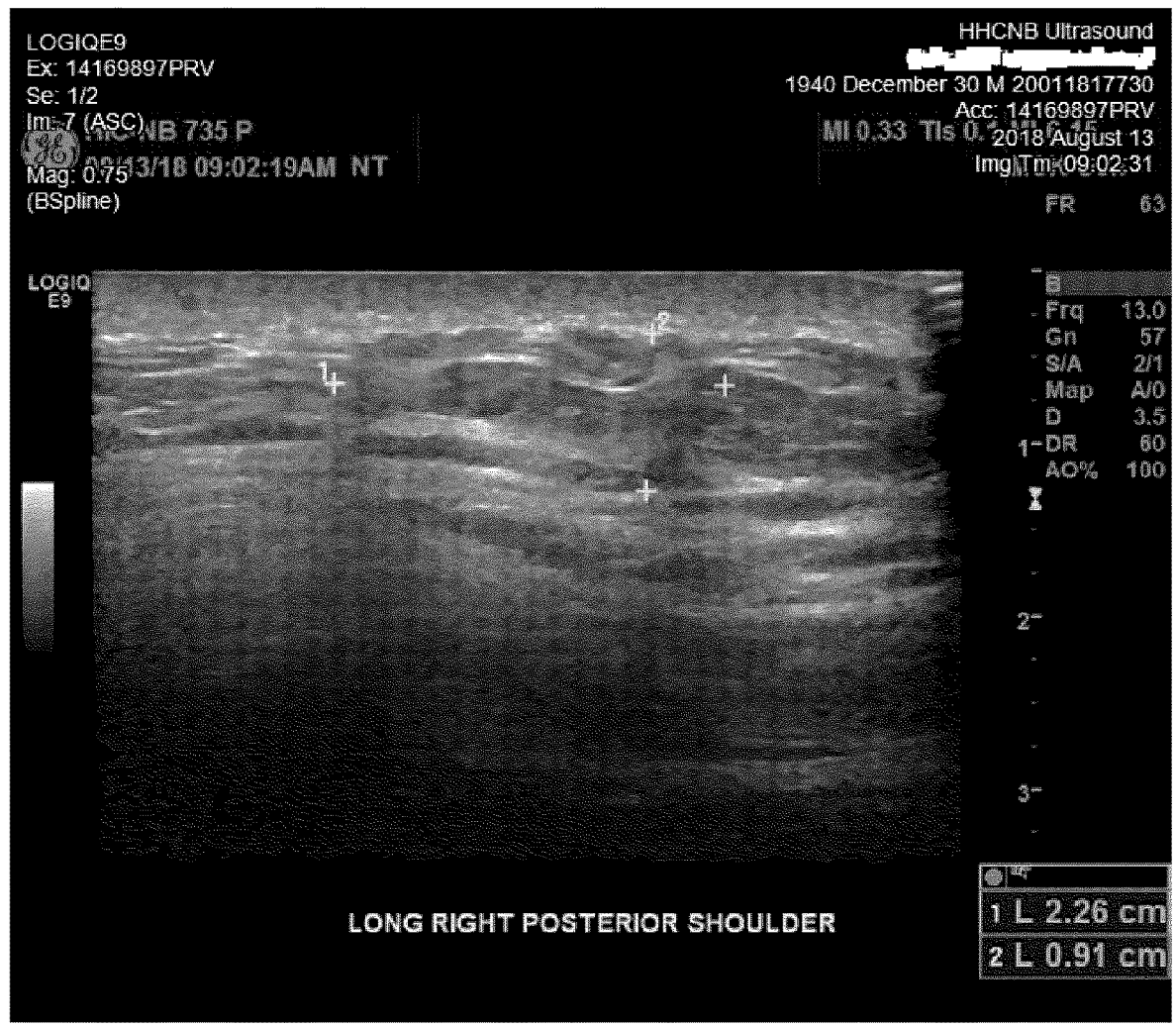
FIG. 5A is an ultrasound of the right upper back of Patient 4 before injection.
Figure 5B:
FIG. 5B is an ultrasound of the right upper back of Patient 4 after injection as described in Example 3.
Figure 6:
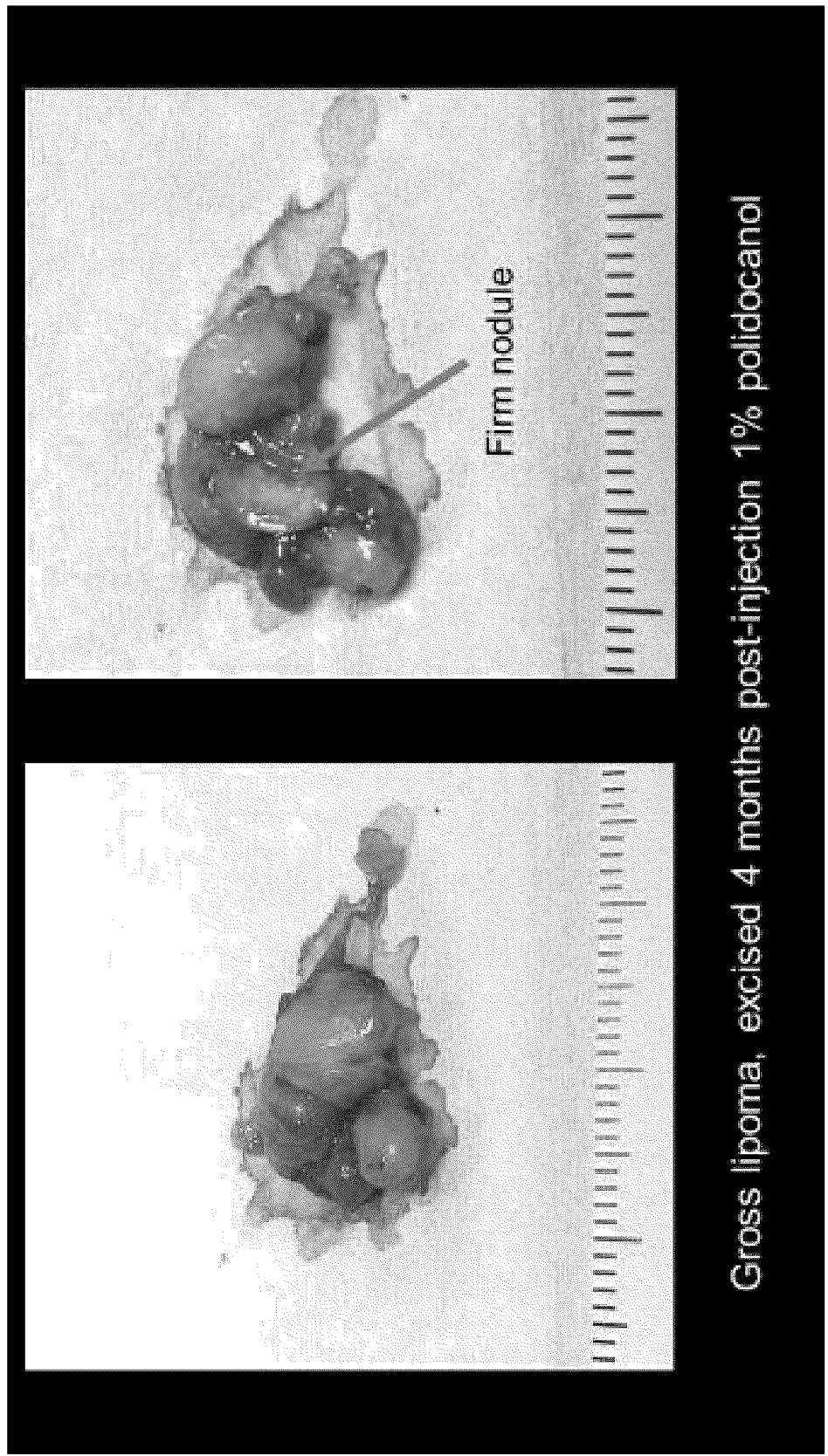
FIG. 6 is a photograph of a lipoma removed from the right forearm 4 four months after injection as described in Example 3.
Figure 7:
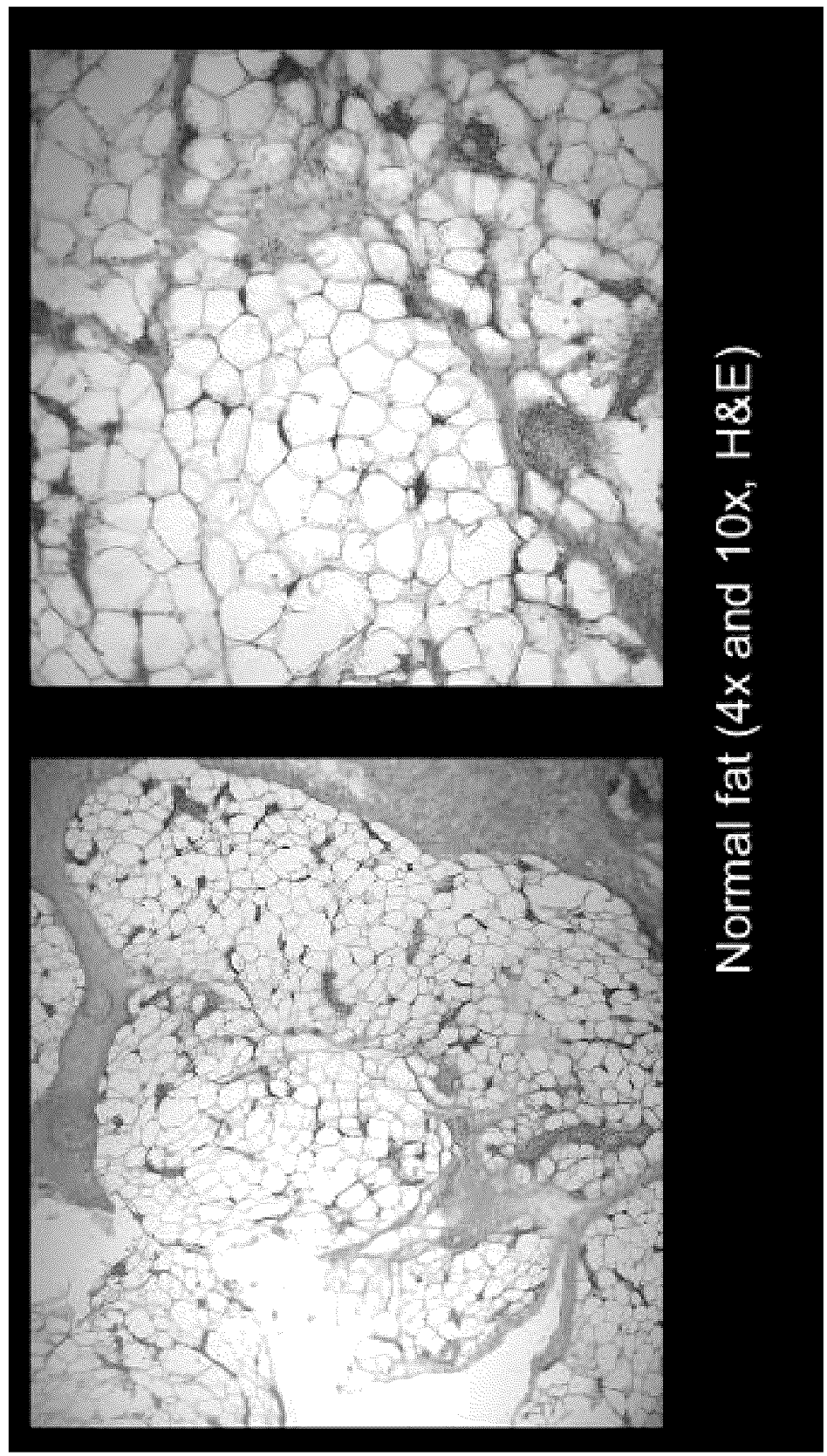
FIG. 7 is an enlargement of a photograph of normal fat.
Figure 8:
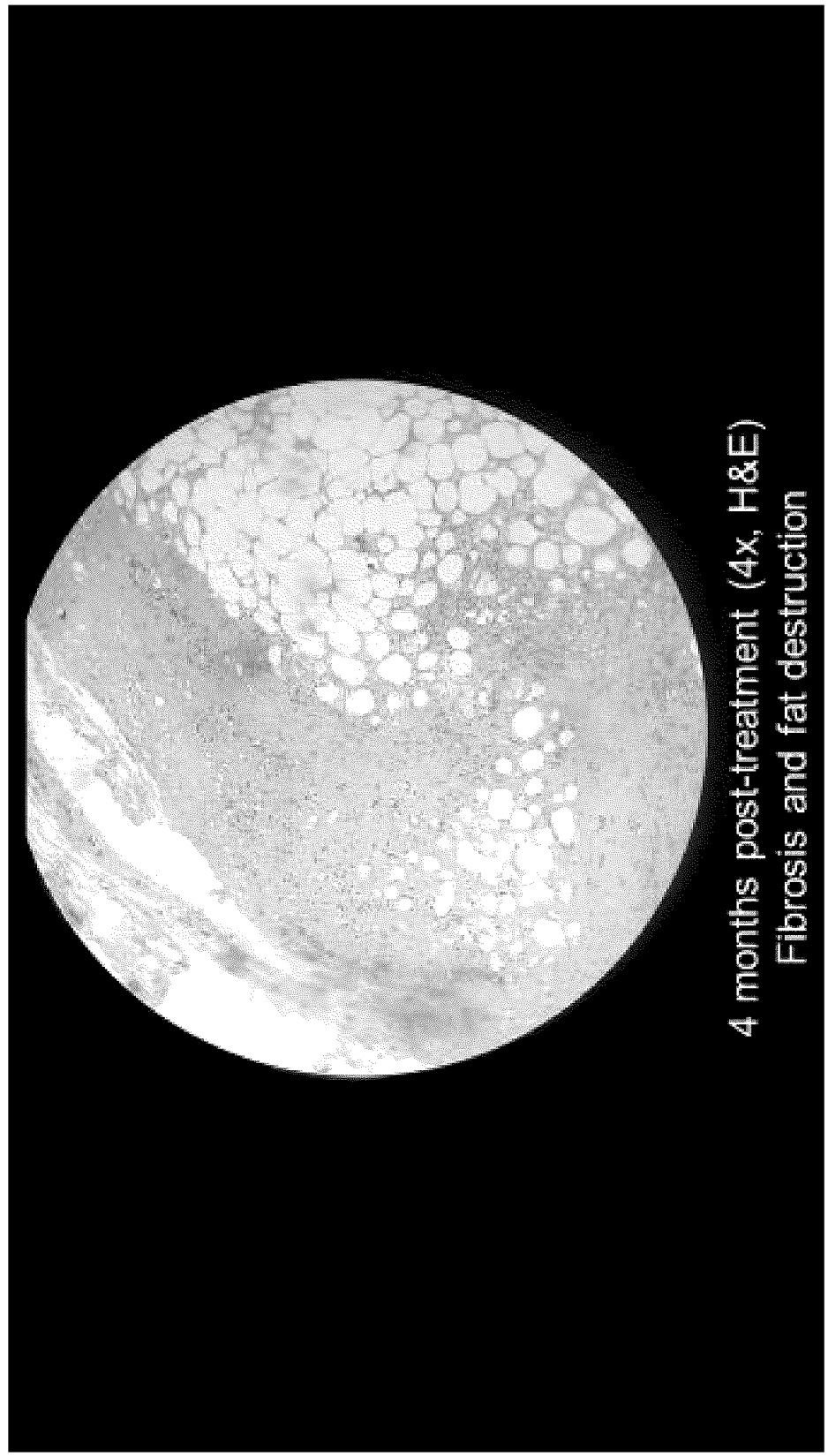
FIG. 8 is an enlargement of a photograph of a portion of the lipoma removed from the right forearm of patient 4 four months after injection as described in Example 3.
Figure 9:
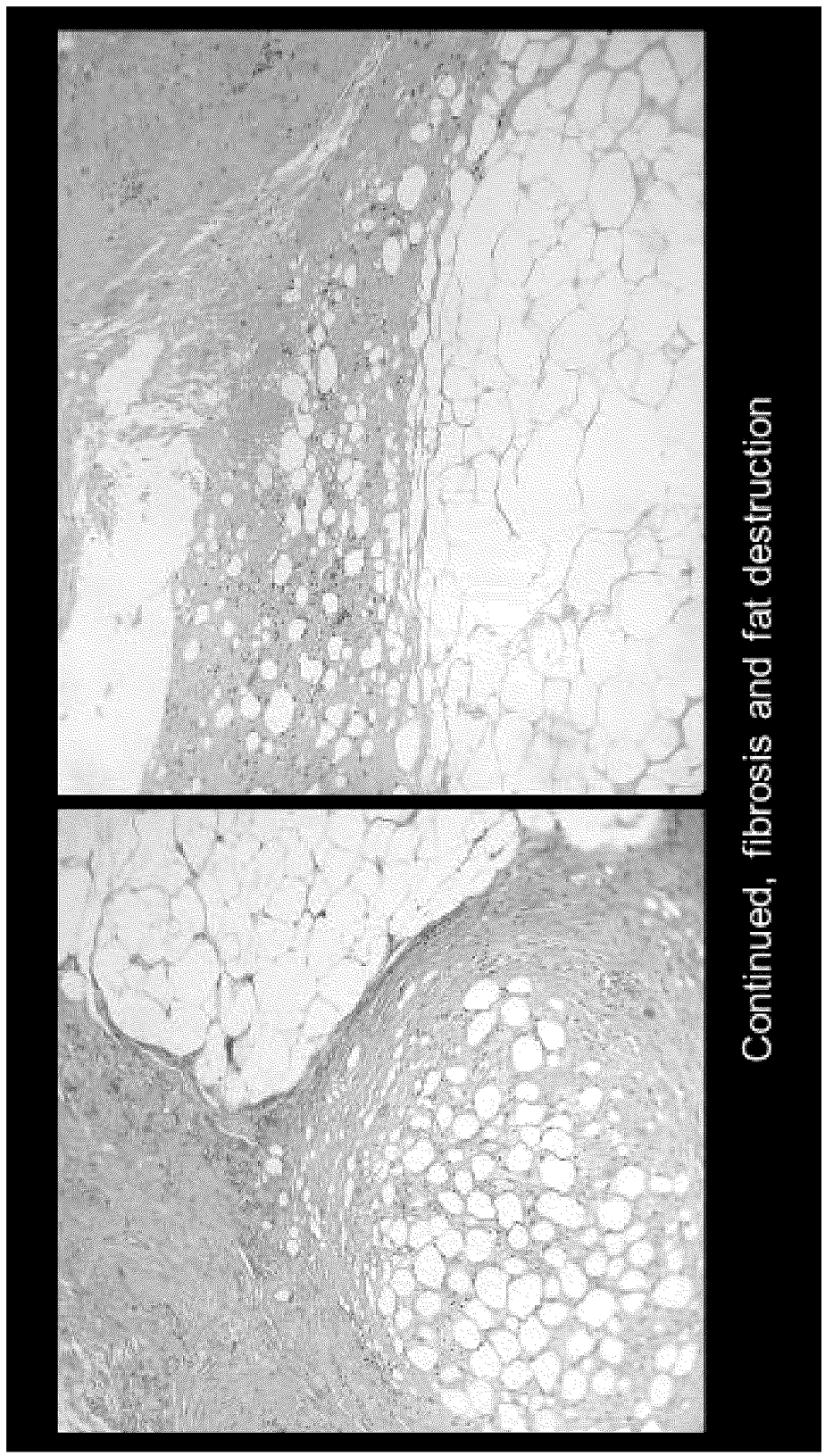
FIG. 9 is another enlargement of a photograph of a portion of the lipoma removed from the right forearm of patient 4 four months after injection as described in Example 3.
Figure 10A:
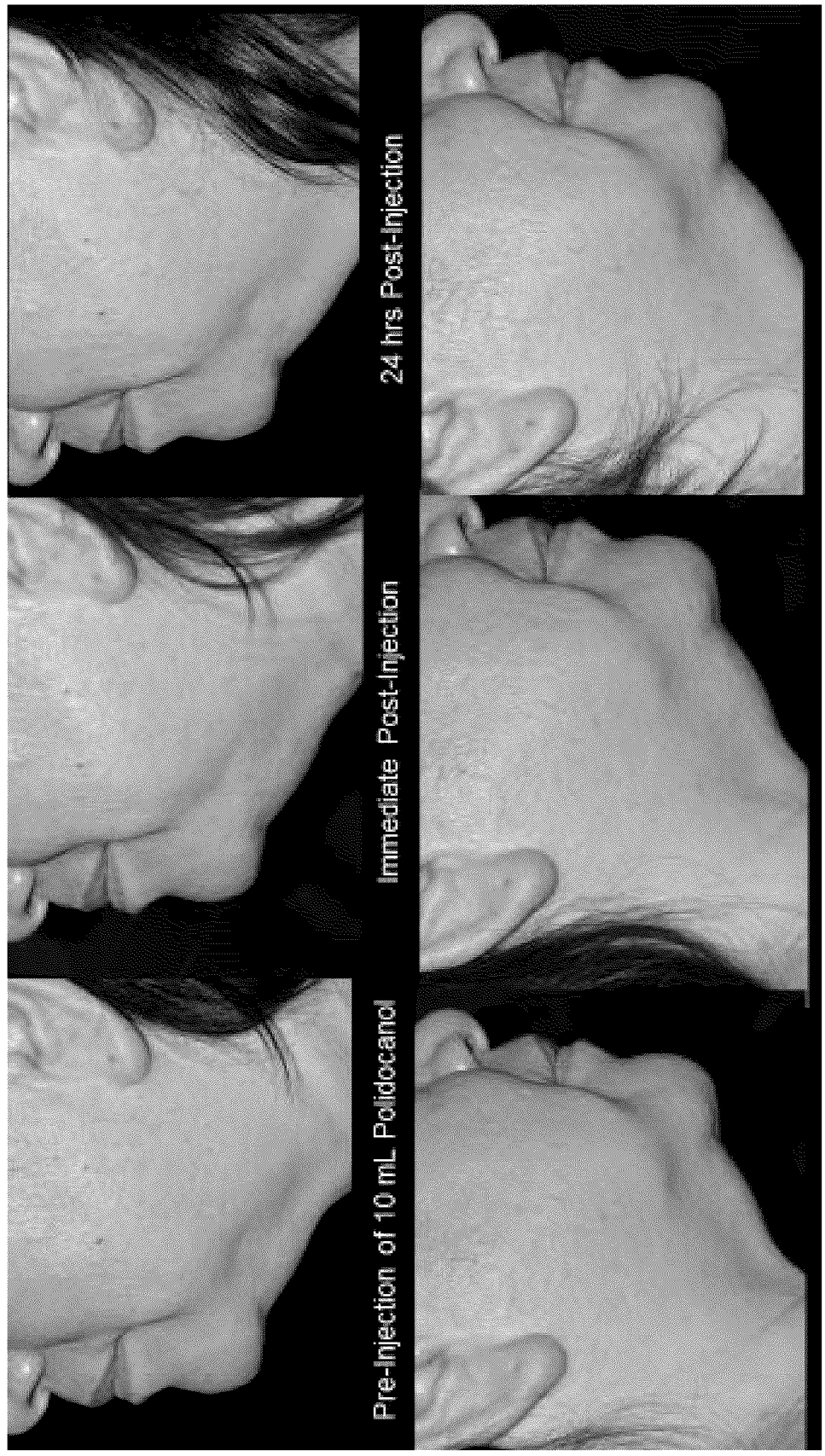
FIGS. 10A and 10B are photographs of the injection site of the patient of Example 7 before injection and 24 hours after injections.
Figure 10B:

The pharmaceutical compositions and methods described herein are useful for fat reduction, in particular the reduction of adipose tissue and the reduction in size of lipomas.

The pharmaceutical compositions described herein may comprise any suitable alcohol. The alcohol may comprise a simple straight chain or branched alcohol such as methanol ($CH_3OH$), ethanol ($CH_3CH_2OH$), propanol ($CH_3CH_2CH_2OH$), isopropanol (($CH_3)_2CHOH$), butanol ($CH_3CH_2CH_2CH_2OH$), branched butyl alcohols, pentanol ($CH_3CH_2CH_2CH_2CH_2OH$), branched pentyl alcohols, hexanol ($CH_3CH_2CH_2CH_2CH_2CH_2OH$), branched hexyl alcohols, heptanol ($CH_3CH_2CH_2CH_2CH_2CH_2CH_2OH$), branched heptyl alcohols, octanol ($CH_3CH_2CH_2CH_2CH_2CH_2CH_2CH_2OH$), branched octyl alcohols, or any combination thereof. The alcohol may be polyhydric, such as ethylene glycol or any other alkyl chain substituted with two or more hydroxyl groups. In some embodiments, the alcohol may comprise an unsaturated aliphatic alcohol, such as 1-butene-4-ol, or any other unsaturated carbon chain substituted with an —OH functional group at a non-alkenyl carbon atom. Some embodiments include an alicyclic alcohol, such as cyclopentanol, cyclohexanol, hydroxymethylcyclopentane and the like.

The alcohol may also comprise a polyethylene glycol portion. For example, the alcohol may be ($C_{1-20}$ alkyl)-($OCH_2CH_2$)$_{1-20}$—OH, e.g., ($C_{8-14}$ alkyl)-($OCH_2CH_2$)$_{6-12}$—OH or ($C_{10-12}$ alkyl)-($OCH_2CH_2$)$_{8-10}$—OH. For example, the alcohol may be polidocanol. The chemical structure of polidocanol is shown below in Formula 1.

Formula 1

Any of the above alcohols may be combined. For example, the pharmaceutical composition may comprise a combination of ethanol and polidocanol.

The pharmaceutical compositions described herein may include any suitable concentration of the alcohol. For the purposes of this disclosure, concentrations are expressed in terms of milligrams per milliliter of solution (mg/mL). It is understood to those of ordinary skill in the art that 1 mg/mL is equivalent to a concentration of 0.1% and 10 mg/mL is equivalent to 1%, etc. In the present disclosure, 1 mg/mL and 0.1% are considered to be identical descriptions of the concentration of a solution. In some embodiments, the alcohol may be present in a concentration of about 1 mg/mL to about 1000 mg/mL, about 1-10 mg/mL, about 1-100 mg/mL, about 10-100 mg/mL, about 100-1000 mg/mL, about 1-1.5 mg/mL, about 1.5-2 mg/mL, about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about 9-10 mg/mL, about 10-25 mg/mL, about 25-50 mg/mL, about 50-75 mg/mL, about 75-100 mg/mL, about 50-100 mg/mL, about 100-250 mg/mL, about 250-500 mg/mL, about 500-1000 mg/mL, or about any concentration in a range bounded by any of these values. Ranges above that encompass the following concentrations are of particular interest: about 1 mg/mL, about 10 mg/mL and about 100 mg/mL.

When the alcohol is polidocanol, either alone or in combination with another alcohol, such as ethanol, any suitable amount of polidocanol may be present in the pharmaceutical composition, such as about 0.05 mg/mL to about 100 mg/mL, about 5-10 ng/mL, about 0.05-0.1 mg/mL, about 0.1-1 mg/mL, 0.1-0.2 mg/mL, about 0.2-0.3 mg/mL, about 0.3-0.4 mg/mL, about 0.4-0.5 mg/mL, about 0.4-0.6 mg/mL, about 0.5-0.6 mg/mL, about 0.6-0.7 mg/mL, about 0.7-0.8 mg/mL, about 0.8-0.9 mg/mL, about 0.9-1.1 mg/mL, about 0.9-1 mg/mL, about 1-1.5 mg/mL, about 1.5-2 mg/mL, about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about 9-10 mg/mL, about 10-20 mg/mL, about 20-30 mg/mL, about 30-40 mg/mL, about 40-50 mg/mL, about 50-60 mg/mL, about 60-70 mg/mL, about 70-80 mg/mL, about 80-90 mg/mL, about 90-100 mg/mL, about 0.1-5 mg/mL, about 5-10 mg/mL, about 10-25 mg/mL, about 25-50 mg/mL, about 50-75 mg/mL, about 75-100 mg/mL, about 50-100 mg/mL, or about any concentration in a range bounded by any of these values. Ranges above that encompass the following concentrations are of particular interest: about 0.5 mg/mL, about 0.75 mg/mL, about 1 mg/mL, about 2.5 mg/mL, as well as about 5.0 mg/mL.

When the alcohol is ethanol, either alone or in combination with another alcohol, such as polidocanol, any suitable amount of ethanol may be present in the pharmaceutical composition, such as about 0.1-1 mg/mL, about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about 9-10 mg/mL, about 10-20 mg/mL, about 20-30 mg/mL, about 30-40 mg/mL, about 40-50 mg/mL, about 50-60 mg/mL, about 60-70 mg/mL, about 70-80 mg/mL, about 80-90 mg/mL, about 90-100 mg/mL, about 100-200 mg/mL, about 200-300 mg/mL, about 300-400 mg/mL, about 400-500 mg/mL, about 500-600 mg/mL, about 600-700 mg/mL, about 700-800 mg/mL, about 800-900 mg/mL, or about 900-1,000 mg/mL. Ranges above that encompass the following concentrations are of particular interest: about 1 mg/mL, about 10 mg/mL and about 100 mg/mL.

The pharmaceutical compositions described herein may further comprise a steroid, such as alclometasone, amcinonide, betamethasone, clobetasol, clocortolone, desonide, desoximetasone, diflorasone, fluocinolone, fluocinonide, flurandrenolide, fluticasone, halcinonide, halobetasol, hydrocortisone, methylprednisolone, mometasone, prednicarbate, triamcinolone, or a combination thereof. Some embodiments include an injectable steroid. Some embodiments include triamcinolone acetonide (TAC). Any suitable amount of a steroid, e.g., TAC, may be present in the pharmaceutical composition. In some embodiments, the steroid may be present in a concentration of about 0.1 mg/mL to about 100 mg/mL, about 1-10 mg/mL, about 0.1-1 mg/mL, about 0.1-0.2 mg/mL, about 0.2-0.3 mg/mL, about 0.3-0.4 mg/mL, about 0.4-0.5 mg/mL, about 0.4-0.6 mg/mL, about 0.5-0.6 mg/mL, about 0.6-0.7 mg/mL, about 0.7-0.8 mg/mL, about 0.8-0.9 mg/mL, about 0.9-1.1 mg/mL, about 0.9-1 mg/mL, about 1-1.5 mg/mL, about 1.5-2 mg/mL, about 0.1-1 mg/mL, about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about 9-10 mg/mL, about 10-20 mg/mL, about 20-30 mg/mL, about 30-40 mg/mL, about 40-50 mg/mL, about 50-60 mg/mL, about 60-70 mg/mL, about 70-80 mg/mL, about 80-90 mg/mL, about 90-100 mg/mL, about 0.1-10 mg, about 10-25 mg/mL, about 25-50 mg/mL, about 50-75 mg/mL, about 50-100 mg/mL, about 75-100 mg/mL, or about any concentration in a range bounded by any of these values. Ranges above that encompass the following concentrations are of particular interest: about 1 mg/mL about 2.5 mg/mL, about 5 mg/mL, about 7.5 mg/mL, and about 10 mg/mL.

The pharmaceutical compositions described herein may further comprise a bile acid such as, cholic acid, taurocholic acid, glycocholic acid, taurochenodeoxycholic acid, glycochenodeoxycholic acid, chenodeoxycholic acid, deoxycholic acid, lithocholic acid, a combination thereof, or a salt of one or more of these acids. Some embodiments include a bile salt comprising deoxycholate (DC). Any suitable amount of a bile salt, such as DC, may be present in the pharmaceutical composition. In some embodiments, the bile salt may be present in a concentration of about 0.1 mg/mL to about 100 mg/mL, about 0.1-1 mg/mL, about 0.1-0.2 mg/mL, about 0.2-0.3 mg/mL, about 0.3-0.4 mg/mL, about 0.4-0.5 mg/mL, about 0.4-0.6 mg/mL, about 0.5-0.6 mg/mL, about 0.6-0.7 mg/mL, about 0.7-0.8 mg/mL, about 0.8-0.9 mg/mL, about 0.9-1.1 mg/mL, about 0.9-1 mg/mL, about 1-1.5 mg/mL, about 1.5-2 mg/mL, about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about 9-10 mg/mL, about 10-25 mg/mL, about 25-50 mg/mL, about 50-75 mg/mL, about 50-100 mg/mL, about 75-100 mg/mL, or about any concentration in a range bounded by any of these values. Ranges above that encompass the following concentrations are of particular interest: about 1 mg/mL about 2.5 mg/mL, about 5 mg/mL, about 7.5 mg/mL, and about 10 mg/mL.

A pharmaceutical composition comprising an alcohol may further include a detergent, such as a fatty acid (e.g. linoleic acid, α-linolenic acid, palmitic acid, oleic acid, stearic acid), phosphatidyl choline, deoxycholic acid, benzyl alcohol, Some pharmaceutical compositions may further include a dermal filler, such as hyaluronic acid, calcium hydroxylapatite, collagen, poly(methyl methacrylate), poly-1-lactic acid, etc.

The pharmaceutical compositions of the current disclosure may further comprise a dispersing agent. In some embodiments, the dispersing agent may comprise collagenase. Some embodiments include a dispersing agent comprising hyaluronidase.

In some embodiments, an anti-inflammatory compound, such as a non-steroidal anti-inflammatory drug (NSAID), e.g. aspirin, acetaminophen, celecoxib, diclofenac, diflunisal, etodolac, flurbiprofen, ibuprofen, indomethacin, ketoprofen, ketorolac, meloxicam, nabumetone, naproxen, naproxen sodium, oxaprozin, piroxicam, salsalate, sulindac, tolmetin, and vimovo is included in the pharmaceutical composition.

In some embodiments, a numbing or local anesthetic compound, e.g. lidocaine, benzocaine, chloroprocaine, cyclomethycaine, dimethocaine, piperocaine, propoxycaine, procaine, proparacaine, tetracaine, articaine, bupivacaine, cinchocaine, etidocaine, levobupivacaine, mepivacaine, prilocaine, ropivacaine, trimecaine, and spilanthol is included in the pharmaceutical composition. Some embodiments include pretreating the area to be injected with a numbing or local anesthetic compound.

Some embodiments of the present disclosure include methods for removing fat from an animal or a human patient. In biology, "fat" is a term that is associated with adipose tissue, which is a loose connective tissue composed mainly of adipocytes. The term "fat" as used herein, is understood to include all types of animal or human body fat, including visceral (abdominal) fat, cellulite, subcutaneous fat, intramuscular fat, white fat (white adipose tissue, or WAT), brown fat (brown adipose tissue, or BAT), beige (or brite) fat, intrathecal fat, ectopic fat, breast tissue, submental fat, and the like.

The patient may be a human being, or an animal, such as a reptile, bird, or mammal (e.g. a dog, a cat, a rabbit, a hamster, a guinea pig, a horse, cattle, goats, sheep, etc.)

A lipoma is a slow-growing mass of fat cells that is often situated between skin and the underlying muscle layer. A lipoma is considered to be a benign tumor. Lipomas are soft to the touch, painless, and move readily with light finger pressure. Subtypes of lipomas include adenolipomas, angiolipoleiomyomas, angiolipomas, chondroid lipomas, hibernomas, spindle-cell lipomas, and superficial subcutaneous lipomas. Lipomas are normally removed by excision, or liposuction.

It is envisioned that a human patient or an owner of an animal patient may desire reduction of fat from one or more regions of the body including, but not limited to, visible fat bulges in the submental area, brow area, suborbital area, cheeks, ears, neck, chin, eyelids, lips, thighs, abdomen, flank, bra-line, back, buttocks, arms (in particular, upper arms), shoulders, armpits, hips, calves, ankles, chest, and breasts. A method for the reduction of fat in an animal or a human patient using a pharmaceutical composition of the present disclosure is also described herein. It is anticipated, using procedures known in the art, that the pharmaceutical compositions described herein may be readily formulated into an injectable, liquid medication. Such a formulation may be delivered by needle or cannula to an animal or a human patient in need thereof.

The method for delivering the pharmaceutical compositions described herein to an animal or a human patient in need thereof may also include the known technique of "foam sclerotherapy." In foam sclerotherapy, air is introduced into an injectable solution prior to administration, causing the solution to "foam," which has been demonstrated to enhance penetration and efficacy of the injectable solution at the affected surface area, thereby reducing the overall dosage of injectable drug solution needed.

The method of administration of the pharmaceutical compositions described herein is injection. In some embodiments, the injection is a subcutaneous injection. Other methods of injection include intramuscular, intrathecal, and intralesional. In the case of lipomas, which are benign collections of subcutaneous, intramuscular, or intrathecal fat, intralesional injection performed under imaging is of particular interest. In some embodiments, the imaging method includes fluoroscopy, ultrasound, or other radiologic imaging method.

In some embodiments, the method of removing or reducing fat further comprises the administration of a neurotoxin. Some examples of the method include the administration of a botulinum neurotoxin (BoNT). In some cases, the botulinum neurotoxin is botulinum toxin A. In other embodiments, the botulinum neurotoxin is botulinum toxin B. The neurotoxin may be injected by any suitable method, including but not limited to subcutaneous, intramuscular, intrathecal and intralesional injection. In some embodiments, the neurotoxin is administered concurrently with the pharmaceutical compositions described herein. Some examples include administration of the neurotoxin prior to administration of the pharmaceutical compositions described herein. In some cases, the neurotoxin is administered after the administration of the pharmaceutical compositions described herein.

A patient to be treated may be given a preliminary examination to determine the general health of the patient, whether the patient is sufficiently healthy to receive the injections, and to assess the fat deposit to determine whether treatment is appropriate. Some kinds of fat deposits, such as lipomas, may be confirmed by ultrasound and/or physical examination.

Each fat deposit to be treated may be measured using a ruler or some other method and may be photographed. A fat deposit may have any size that makes it a suitable candidate for treatment. For example, the skin over the fat deposit may have an area of 0.1-1 $cm^2$, about 1-2 $cm^2$, about 2-3 $cm^2$, about 3-4 $cm^2$, about 4-5 $cm^2$, about 5-6 $cm^2$, about 6-7 $cm^2$, about 7-8 $cm^2$, about 8-9 $cm^2$, about 9-10 $cm^2$, about 10-11 $cm^2$, about 11-12 $cm^2$, about 12-13 $cm^2$, about 13-14 $cm^2$, about 14-15 $cm^2$, about 15-16 $cm^2$, about 16-17 $cm^2$, about 17-18 $cm^2$, about 18-19 $cm^2$, about 19-20 $cm^2$, about 0.1-5 $cm^2$, about 5-10 $cm^2$, about 10-15 $cm^2$, about 15-20 $cm^2$, about 20-25 $cm^2$, about 25-30 $cm^2$, about 30-35 $cm^2$, about 35-40 $cm^2$, about 40-45 $cm^2$, about 45-50 $cm^2$, about 50-55 $cm^2$, about 55-60 $cm^2$, about 60-65 $cm^2$, about 65-70 $cm^2$, about 70-75 $cm^2$, about 75-80 $cm^2$, about 80-85 $cm^2$, about 85-90 $cm^2$, about 90-95 $cm^2$, about 95-100 $cm^2$, about 0.1-25 $cm^2$, about 25-50 $cm^2$, about 50-75 $cm^2$, or about 75-100 $cm.^2$ The fat deposit may have any weight that is treatable by the methods described herein, such as about 0.1-10 g, about 10-20 g, about 20-30 g, about 30-40 g, about 40-50 g, about 50-60 g, about 60-70 g, about 70-80 g, about 80-90 g, about 90-100 g, about 10-100 g, about 100-110 g, about 110-120 g, about 120-130 g, about 130-140 g, about 140-150 g, about 150-160 g, about 160-170 g, about 170-180 g, about 180-190 g, about 190-200 g, about 10-100 g, about 100-200 g, about 200-300 g, about 300-400 g, about 400-500 g, about 500-600 g, about 600-700 g, about 700-800 g, about 800-900 g, about 900-1,000 g, about 1-2 kg, about 2-3 kg, about 3-4 kg, about 4-5 kg, about 5-6 kg, about 6-7 kg, about 7-8 kg, about 8-9 kg, about 9-10 kg, about 10-11 kg, about 11-12 kg, about 12-13 kg, about 13-14 kg, about 14-15 kg, about 15-16 kg, about 16-17 kg, about 17-18 kg, about 18-19 kg, about 19-20 kg, about 0.01-1 kg, about 1-5 kg, about 5-10 kg, or about 10-20 kg.

Prior to injection, the skin above the fat deposit is cleansed with, e.g., an isopropyl alcohol swab. All injections are made directly into the fat deposit. For smaller fat deposits (<2 cm in diameter), the fat deposit may be pinched and elevated (using thumb and forefinger) prior to injection. For larger fat deposits (>2 cm in diameter), injection may be done directly without pinching.

The pharmaceutical compositions described herein may be administered in any suitable injection volume. In some embodiments, the injection volume for a single injection may be about 0.1 mL to about 2 mL, about 0.1-1 mL, about 0.1-0.2 mL, about 0.2-0.3 mL, about 0.3-0.4 mL, about 0.4-0.5 mL, about 0.4-0.6 mL, about 0.5-0.6 mL, about 0.6-0.7 mL, about 0.7-0.8 mL, about 0.8-0.9 mL, about 0.9-1.1 mL, about 0.9-1 mL, about 1-1.5 mL, about 1.5-2 mL, about 1-2 mL, or about any injection volume in a range bounded by any of these values. Ranges above that encompass the following concentrations are of particular interest: about 0.1 mL, about 0.5 mL, and about 1 mL.

The pharmaceutical compositions described herein may be administered in any suitable injection volume described above at a spacing distance of approximately every 0.5-2 cm apart. In some embodiments, the spacing distance may be every 0.5-1 cm apart. Some examples include injecting the animal or the human patient in need thereof with a pharmaceutical composition described herein about every 0.5-0.6 cm, about every 0.6-0.7 cm, about every 0.7-0.8 cm, about every 0.8-0.9 cm, about every 0.9-1 cm, about every 1-1.1 cm, about every 1.1-1.2 cm, about every 1.2-1.3 cm, about every 1.3-1.4 cm, about every 1.4-1.5 cm, about every 1.5-1.6 cm, about every 1.6-1.7 cm, about every 1.7-1.8 cm, about every 1.8-1.9 cm, about every 1.9-2 cm, about every 0.5-1 cm, about every 1-1.5 cm, about every 1.5-2 cm, or any spacing distance in a range bounded by any of these values.

The total volume of the pharmaceutical formulation delivered to the animal or human patient in need thereof, and the total number of injections required, will vary with the total area of subcutaneous fat or lesion volume in need of treatment. For example, about 0.1-20 mL, about 2-8 mL, 0.1-1 mL, about 1-2 mL, about 2-3 mL, about 3-4 mL, about 4-5 mL, about 5-6 mL, about 6-7 mL, about 7-8 mL, about 8-9 mL, about 9-10 mL, about 10-11 mL, about 11-12 mL, about 12-13 mL, about 13-14 mL, about 14-15 mL, about 15-16 mL, about 16-17 mL, about 17-18 mL, about 18-19 mL, about 19-20 mL, about 0.01-5 mL, about 5-10 mL, about 10-15 mL, or about 15-20 mL of the pharmaceutical formulation may be injected during one session of treatment.

The total amount of the pharmaceutical composition delivered per fat volume may be about 0.1-2,000 mg/cm$^3$, or any suitable amount. In some embodiments, the amount may be 0.1-1 mg/cm$^3$, 0.1-1 mg/cm$^3$, about 1-2 mg/cm$^3$, about 2-3 mg/cm$^3$, about 3-4 mg/cm$^3$, about 4-5 mg/cm$^3$, about 5-6 mg/cm$^3$, about 6-7 mg/cm$^3$, about 7-8 mg/cm$^3$, about 8-9 mg/cm$^3$, about 9-10 mg/cm$^3$, about 10-20 mg/cm$^3$, about 20-30 mg/cm$^3$, about 30-40 mg/cm$^3$, about 40-50 mg/cm$^3$, about 50-60 mg/cm$^3$, about 60-70 mg/cm$^3$, about 70-80 mg/cm$^3$, about 80-90 mg/cm$^3$, about 90-100 mg/cm$^3$, about 100-200 mg/cm$^3$, about 200-300 mg/cm$^3$, about 300-400 mg/cm$^3$, about 400-500 mg/cm$^3$, about 500-600 mg/cm$^3$, about 600-700 mg/cm$^3$, about 700-800 mg/cm$^3$, about 800-900 mg/cm$^3$, about 900-1,000 mg/cm$^3$, about 1,000-1,100 mg/cm$^3$, about 1,100-1,200 mg/cm$^3$, about 1,200-1,300 mg/cm$^3$, about 1,300-1,400 mg/cm$^3$, about 1,400-1,500 mg/cm$^3$, about 1,500-1,600 mg/cm$^3$, about 1,600-1,700 mg/cm$^3$, about 1,700-1,800 mg/cm$^3$, about 1,800-1,900 mg/cm$^3$, about 1,900-2,000 mg/cm$^3$, about 0.1-3 mg/cm$^3$, 3-5 mg/cm$^3$, 5-10 mg/cm$^3$, 10-50 mg/cm$^3$, 50-100 mg/cm$^3$, 100-400 mg/cm$^3$, 400-600 mg/cm$^3$, 600-1000 mg/cm$^3$, 1000-1500 mg/cm$^3$, 1500-2000 mg/cm$^3$, or about any total amount in a range bounded by any of these values. Ranges above that encompass the following amounts are of particular interest: about 4 mg/cm$^3$ and about 500 mg/cm$^3$.

Within seconds or minutes following completion of a treatment session, the area where the injections are given may be examined by the physician. In some embodiments, the patients may report minimal to no tenderness, burning or pain. In some embodiments, the patients may report less tenderness, burning or pain, than was or would be observed with another treatment, such as propylene glycol/polidocanol, glycerin/polidocanol, or deoxycholic acid (e.g. Kybella®). In some embodiments, minimal to no skin redness may be observed. In some embodiments, less skin redness is observed than was or would be observed with another treatment such as propylene glycol/polidocanol, glycerin/polidocanol, or deoxycholic acid (e.g. Kybella®). In some embodiments, minimal to no edema may be observed. In some embodiments, less edema is observed than was or would be observed with another treatment such as propylene glycol/polidocanol, glycerin/polidocanol, or deoxycholic acid (e.g. Kybella®).

Approximately, 1, 2, 3, 4, or 5 days after injection, any swelling or edema present (as observed by patient or physician) immediately following injection, if present, may be reduced or resolved. Patients may report minimal to no tenderness 1, 2, 3, 4, or 5 days after treatment. Minimal to no bruising is reported by all patients; in those patients with minimal bruising, it is transient and resolves within several days. No blisters, ulceration or numbness are reported.

The patient may receive a single injection or set of injections in a single treatment or office visit, or the patient may be treated with one or more injections on multiple occasions, such as injections once every 1-12 weeks, once every 2 weeks, once a month, or once every other month. In some embodiments, a patient may receive 1, 2, 3, 4, 5, or 6 total treatments. In some examples, the total time of treatment is 1-12 weeks, 1-4 weeks, 1-8 weeks, 1-2 weeks, 1 week, 2 weeks, 3 weeks, 4 weeks, 5 weeks, 6 weeks, 7 weeks, 8 weeks, 9 week, 10 weeks, 11 weeks, 12 weeks, or any number of weeks required to treat the patient in need thereof.

Some embodiments include one or more follow up examinations of the animal or the human patients in need of treatment. In some cases, the follow up examinations may be at 1, 2, 3, 4, 5, 6, 7, 8, 9, or 10 days, 2 weeks, 3 weeks, 1 month, 2 months, 0-2 months, 2-4 months, 4-6 months, 6-8 months, 8-10 months, 10-12 months, and/or 1-2 years after last injection, or longer. In some embodiments, at the follow up examination, no swelling is observed in the area where the injections occurred. In some embodiments, at the follow up examination, no redness is observed in the area where the injections occurred. In some embodiments, at the follow up examination, no ulceration is observed in the area where the injections occurred. In some embodiments, at the follow up examination, no bruising is observed in the area where the injections occurred. In some embodiments, at the follow up examination, no or other changes to the skin are observed in the area where the injections occurred.

In some embodiments, 2-4 weeks after treatment, no swelling is observed in the area where the injections occurred. In some embodiments, 2-4 weeks aftertreatment, no redness is observed in the area where the injections occurred. In some embodiments, 2-4 weeks after treatment, no ulceration is observed in the area where the injections occurred. In some embodiments, 2-4 weeks after treatment, no bruising is observed in the area where the injections occurred. In some embodiments, 2-4 weeks after treatment, no or other changes to the skin are observed in the area where the injections occurred.

As a result of the injections, the appearance of the fat deposit may be improved. This improvement may be in observed by the patient or the physician treating the patient. The patient may report that the appearance of the fat deposit, in terms of aesthetics or size, to be "somewhat improved," "improved," or "much improved." On a numerical scale reported by the patient, an improvement of at least about 10%, at least about 20%, at least about 30%, at least about 40%, at least about 50%, at least about 60%, at least about 70%, at least about 80%, at least about 90%, 10-20%, about 20-30%, about 30-40%, about 40-50%, about 50-60%, about 60-70%, about 70-80%, about 80-90%, about 90-100%, about 10-40%, about 40-70%, or about 70-100% may be reported.

The physician treating the patient may report that the appearance of the fat deposit, in terms of aesthetics or size, to be "somewhat improved," "improved," or "much improved." On a numerical scale reported by the physician treating the patient, an improvement of at least about 10%, at least about 20%, at least about 30%, at least about 40%, at least about 50%, at least about 60%, at least about 70%, at least about 80%, at least about 90%, 10-20%, about 20-30%, about 30-40%, about 40-50%, about 50-60%, about 60-70%, about 70-80%, about 80-90%, about 90-100%, about 10-40%, about 40-70%, or about 70-100% may be reported.

Additionally, or alternatively, as a result of the injections, the area, volume, mass, or weight of the fat deposit may be reduced, e.g. by at least about 10%, at least about 20%, at least about 30%, at least about 40%, at least about 50%, at least about 60%, at least about 70%, at least about 80%, at least about 90%, about 10-20%, about 20-30%, about 30-40%, about 40-50%, about 50-60%, about 60-70%, about 70-80%, about 80-90%, about 90-100%, about 10-40%, about 40-70%, about 70-100%, or reduced by about 0.1-1 cm$^2$, about 1-2 cm$^2$, about 2-3 cm$^2$, about 3-4 cm$^2$, about 4-5 cm$^2$, about 5-6 cm$^2$, about 6-7 cm$^2$, about 7-8 cm$^2$, about 8-9 cm$^2$, about 9-10 cm$^2$, about 10-11 cm$^2$, about 11-12 cm$^2$, about 12-13 cm$^2$, about 13-14 cm$^2$, about 14-15 cm$^2$, about 15-16 cm$^2$, about 16-17 cm$^2$, about 17-18 cm$^2$, about 18-19 cm$^2$, about 19-20 cm$^2$, about 0.1-5 cm$^2$, about 5-10 cm$^2$, about 10-15 cm$^2$, about 15-20 cm$^2$, about 20-25 cm$^2$, about 25-30 cm$^2$, about 30-35 cm$^2$, about 35-40 cm$^2$, about 40-45 cm$^2$, about 45-50 cm$^2$, about 50-55 cm$^2$, about 55-60 cm$^2$, about 60-65 cm$^2$, about 65-70 cm$^2$, about 70-75 cm$^2$, about 75-80 cm$^2$, about 80-85 cm$^2$, about 85-90 cm$^2$, about 90-95 cm$^2$, about 95-100 cm$^2$, about 0.1-25 cm$^2$, about 25-50 cm$^2$, about 50-75 cm$^2$, or about 75-100 cm,$^2$ or reduced by about 0.1-10 cm$^3$, about 10-20 cm$^3$, about 20-30 cm$^3$, about 30-40 cm$^3$, about 40-50 cm$^3$, about 50-60 cm$^3$, about 60-70 cm$^3$, about 70-80 cm$^3$, about 80-90 cm$^3$, about 90-100 cm$^3$, about 10-100 cm$^3$, about 100-110 cm$^3$, about 110-120 cm$^3$, about 120-130 cm$^3$, about 130-140 cm$^3$, about 140-150 cm$^3$, about 150-160 cm$^3$, about 160-170 cm$^3$, about 170-180 cm$^3$, about 180-190 cm$^3$, about 190-200 cm$^3$, about 10-100 cm$^3$, about 100-200 cm$^3$, about 200-300 cm$^3$, about 300-400 cm$^3$, about 400-500 cm$^3$, about 500-600 cm$^3$, about 600-700 cm$^3$, about 700-800 cm$^3$, about 800-900 cm$^3$, about 900-1,000 cm$^3$, about 1-2 kg, about 2-3 kg, about 3-4 kg, about 4-5 kg, about 5-6 kg, about 6-7 kg, about 7-8 kg, about 8-9 kg, about 9-10 kg, about 10-11 kg, about 11-12 kg, about 12-13 kg, about 13-14 kg, about 14-15 kg, about 15-16 kg, about 16-17 kg, about 17-18 kg, about 18-19 kg, about 19-20 kg, about 0.01-1 kg, about 1-5 kg, about 5-10 kg, or about 10-20 kg.

EXAMPLES

Example 1: Preparation of Pharmaceutical Composition Z

Polidocanol (10 mg), triamcinolone acetonide (2 mg) and deoxycholate (2 mg) are dissolved in 2 mL of deionized water with 5% (v/v) ethanol to prepare an injectable solution. The solution is adjusted to pH 6.5-8.0 using disodium hydrogen phosphate dihydrate and potassium dihydrogen phosphate.

Example 2: Submental Fat Reduction Using Pharmaceutical Composition Z

Human patient X, presenting submental fullness, is treated over a period of 12 weeks with pharmaceutical composition Z. On day 1 of treatment, a rectangular treatment area of 5 cm by 4 cm is measured and photographed. Injections are made 1 cm apart, thus comprising a total of 30 total injection sites. Into each site, 0.05 mL of pharmaceutical composition Z is injected. Patient X returns 2 weeks later, presenting no adverse side effects, is measured and photographed, and receives another regimen of 30 injections containing 0.05 mL of pharmaceutical composition Z. Patient X returns after 4 weeks, 6 weeks, 8 weeks, 10 weeks and 12 weeks for identical measurements, photographs and treatments. At each visit, starting with week 2, patient X and the treating physician rate the level of improvement as some/moderately better (1-grade composite response) or significant/a great deal better (2-grade composite response). The measurements of the submental fat treatment show patient X incurs a reduction of 50% of the original submental fullness in 4 weeks, 70% in 8 weeks, and 85% in 12 weeks after the first treatment session.

Example 3: Lipoma Treatment Using 5% (v/v) Ethanol and 1% Polidocanol

Six patients presenting lipomas were given a preliminary examination. In general, the lipomas were discrete, mobile, non-tender subcutaneous nodules or benign tumors, and none of the patients had undergone any treatment or procedure with regard to the lipoma. Several lipomas were confirmed by ultrasound, and all lipomas were confirmed by physical examination. Each lipoma to be treated was measured using a ruler and photographed, then the skin above the lipoma was cleansed with an isopropyl alcohol swab. 0.5 cc (0.5 mL) of 5% ethanol/1% polidocanol (in water, pH adjusted to 6.5-8 using phosphate buffer, "Et/PD") was injected into the lipoma, and repeated injections into the lipoma were spaced 1 cm apart. All injections were made directly into the lipoma. For smaller lipomas (<2 cm in diameter), the lipoma was pinched and elevated (using thumb and forefinger) prior to injection. For larger lipomas (>2 cm in diameter), injection was done directly without pinching. Depending on lipoma size, 2 mL to 8 mL of Et/PD was injected during one session of treatment. Treatment sessions were spaced at least 2 weeks apart.

Immediate Outcomes (Physician Examination):

Within seconds or minutes following completion of a treatment session, the area where the injections were given was examined by the physician. Two patients reported moderate pain immediately following the first injection, but no pain for subsequent injections. The other four patients reported minimal to no tenderness, burning or pain. Minimal to no skin redness was observed in any patient. Mild to no edema (swelling) was observed in all patients.

Short Term Outcomes (within Several Days of Treatment, Patient Reported):

Patients reported minimal to no tenderness 1-5 days after treatment. In those patients showing edema immediately following the treatment session, the swelling is resolved within several days. Moderate bruising was reported by two patients, and minimal to no bruising was reported by four patients; in those patients with bruising, it was transient and resolved within several days. No blisters, ulceration or numbness are reported.

Short Term Outcomes (within Several Days of Treatment, Physician Examination):

Patients are examined 1-5 days after treatment by the treating physician. Minimal redness is observed. Swelling is minimal and proportionate to the injected volume only. No skin surface changes, no ulceration, and no blistering is observed in any patient. Minimal to no bruising is observed.

Longer Term Outcomes (2 Weeks or Longer after Treatment, Physician Examination):

Patients are examined 2-4 weeks after treatment by the treating physician. Each lipoma treated is measured using a ruler and photographed. No swelling, redness, ulceration, bruising, or other changes to the skin above the lipoma is observed. Shrinkage is observed in a majority of the lipomas treated. Tables 1-3 and FIGS. 1-10 depict the results achieved in six patients. The treated lipomas are observed have physical characteristics consistent with the original presentation, being discrete, mobile and non-tender.

The following embodiments are specifically contemplated:

Embodiment 1

A method of reducing a fat deposit comprising injecting a pharmaceutical composition into the fat deposit, wherein the pharmaceutical composition comprises an alcohol, wherein the method is effective in reducing the weight or volume of the fat deposit.

Embodiment 2

The method of embodiment 1, wherein the alcohol is polidocanol.

Embodiment 3

The method of embodiment 1, wherein the alcohol comprises ethanol.

Embodiment 4

The method of embodiment 3, wherein the pharmaceutical composition further comprises polidocanol.

Embodiment 5

The method of embodiment 1, 2, 3, or 4, further comprising a steroid.

Embodiment 6

The method of embodiment 1, 2, 3, 4, or 5, further comprising a bile salt.

Embodiment 7

The method of embodiment 1, 2, 3, 4, 5, or 6, further comprising a detergent.

Embodiment 8

The method of embodiment 1, 2, 3, 4, 5, 6, or 7, further comprising a dermal filler.

Embodiment 9

The method of embodiment 1, 2, 3, 4, 5, 6, 7, or 8, further comprising a neurotoxin.

Embodiment 10

The method of embodiment 1, 2, 3, 4, 5, 6, 7, 8, or 9, wherein the fat deposit is a lipoma.

Embodiment 11

The method of embodiment 1, 2, 3, 4, 5, 6, 7, 8, or 9, wherein the fat deposit is cellulite.

Embodiment 12

The method of embodiment 1, 2, 3, 4, 5, 6, 7, 8, or 9, wherein the fat deposit is on a human head.

Embodiment 13

The method of embodiment 1, 2, 3, 4, 5, 6, 7, 8, or 9, wherein the fat deposit is on a human neck.

Embodiment 14

The method of embodiment 1, 2, 3, 4, 5, 6, 7, 8, or 9, wherein the fat deposit is on a human torso.

Embodiment 15

The method of embodiment 1, 2, 3, 4, 5, 6, 7, 8, or 9, wherein the fat deposit is on a human buttock.

Embodiment 16

The method of embodiment 1, 2, 3, 4, 5, 6, 7, 8, or 9, wherein the fat deposit is on a human leg.

Embodiment 17

The method of embodiment 1, 2, 3, 4, 5, 6, 7, 8, or 9, wherein the fat deposit is on a human foot.

Embodiment 18

The method of embodiment 1, 2, 3, 4, 5, 6, 7, 8, or 9, wherein the fat deposit is on a human arm.

Embodiment 19

The method of embodiment 1, 2, 3, 4, 5, 6, 7, 8, or 9, wherein the fat deposit is on a human hand.

Embodiment 20

The method of embodiment 1, 2, 3, 4, 5, 6, 7, 8, 9, 10, 11, 12, 13, 14, 15, 16, 17, 18, or 19, wherein on a single day, about 1 mg to about 20 mg of the pharmaceutical composition, per cm³ of fat deposit, is injected into the fat deposit.

Embodiment 21

Use of the pharmaceutical composition of embodiment 1, 2, 3, 4, 5, 6, 7, 8, 9, 10, 11, 12, 13, 14, 15, 16, 17, 18, 19, or 20 in the manufacture of a medicament for reducing a fat deposit.

Embodiment A1

A method of reducing fat comprising subcutaneously injecting a pharmaceutical composition into a fat deposit of an animal, wherein the pharmaceutical composition comprises an ethanol and polidocanol, wherein the method is effective in reducing the weight or volume of the fat deposit.

Embodiment A2

The method of embodiment A1, further comprising a steroid.

Embodiment A3

The method of embodiment A1 or A2, further comprising a bile salt.

Embodiment A4

The method of embodiment A1, A2, or A3, further comprising a detergent.

Embodiment A5

The method of embodiment A1, A2, A3, or A4, further comprising a dermal filler.

Embodiment A6

The method of embodiment A1, A2, A3, A4, or A5, further comprising a neurotoxin.

Embodiment A7

The method of embodiment A1, A2, A3, A4, A5, or A6, wherein the fat deposit is a lipoma.

Embodiment A8

The method of embodiment A1, A2, A3, A4, A5, or A6, wherein the fat deposit is cellulite.

Embodiment A9

The method of embodiment A1, A2, A3, A4, A5, A6, A7, or A8, wherein the fat deposit is on a head.

Embodiment A10

The method of embodiment A1, A2, A3, A4, A5, A6, A7, or A8, wherein the fat deposit is on a neck.

Embodiment A11

The method of embodiment A1, A2, A3, A4, A5, A6, A7, or A8, wherein the fat deposit is on a torso.

Embodiment A12

The method of embodiment A1, A2, A3, A4, A5, A6, A7, or A8, wherein the fat deposit is on a buttock.

Embodiment A13

The method of embodiment A1, A2, A3, A4, A5, A6, A7, or A8, wherein the fat deposit is on a leg.

Embodiment A14

The method of embodiment A1, A2, A3, A4, A5, A6, A7, or A8, wherein the fat deposit is on a foot.

Embodiment A15

The method of embodiment A1, A2, A3, A4, A5, A6, A7, A8, A9, A10, A11, A12, A13, or A14, wherein on a single day, about 1 mg to about 20 mg of the pharmaceutical composition, per cm³ of fat deposit, is injected into the fat deposit.

Embodiment A16

The method of embodiment A1, A2, A3, A4, A5, A6, A7, A8, A9, A10, A11, A12, A13, A14, or A15, wherein the animal is a dog.

Embodiment A17

The method of embodiment A1, A2, A3, A4, A5, A6, A7, A8, A9, A10, A11, A12, A13, A14, or A15, wherein the animal is a cat.

Embodiment A18

The method of embodiment A1, A2, A3, A4, A5, A6, A7, A8, A9, A10, A11, A12, A13, A14, or A15, wherein the animal is a rabbit.

Embodiment A19

The method of embodiment A1, A2, A3, A4, A5, A6, A7, A8, A9, A10, A11, A12, A13, A14, or A15, wherein the animal is a hamster.

Embodiment A20

The method of embodiment A1, A2, A3, A4, A5, A6, A7, A8, A9, A10, A11, A12, A13, A14, or A15, wherein the animal is a Guinea pig.

Embodiment A21

The method of embodiment A1, A2, A3, A4, A5, A6, A7, A8, A9, A10, A11, A12, A13, A14, or A15, wherein the animal is a horse.

Patient Information for Tables 1-3:
Patient 1: 70 year-old woman
Patient 2: 59 year-old woman
Patient 3: 58 year-old man
Patient 4: 78 year-old man
Patient 5: 41 year-old man
Patient 6: 72 year-old woman

TABLE 1

| | | | | | | | | | Interval |
| | | | | | | | | | between |
| | | Pre-tx | Post-tx | | Number | | | | last |
| | | meas. | meas. | | of | | Surface | | tx and |
| | | (cm × | (cm × | | txs/ | | change, | Interval | final |
| | | cm)/ | cm)/ | | Injection | Immediate | redness | Between | meas. |
| Patient | Site | area (cm²) | area (cm²) | % Change | volume (mL) | Pain (1-10) | (anytime) | Other Post-tx side effects | txs (wks) | (wks) |
|---|---|---|---|---|---|---|---|---|---|---|
| 1 | Right elbow | 4 × 4/ 16 | 2.5 × 1.5/ 3.75 | −77 | 2/ 1.5 | 0/10 | mild bruising several days | mild swelling 24 hours | 8 | 15 |
| 1 | Right mid-forearm | 2 × 2/ 4 | 1.2 × 1/ 1.2 | −70 | 2/ 1.5 | 0/10 | none | none | 9 | 14 |
| 1 | Left elbow | 3 × 3/ 9 | 2 × 1/ 2 | −78 | 2/ 1.5 | 4/10 immediate burn then 0/10 | moderate bruising for several days | mild swelling for 36 hours, firm 4 weeks | 3 | 32 |
| 1 | Right wrist | 2 × 2/ 4 | 1 × 1/ 1 | −75 | 2/ 1 | 2/10 immediate burn then 0/10 | none | none | 8 | 15 |
| 1 | Left upper arm | 3.5 × 4/ 14 | 3 × 2.5/ 7.5 | −46 | 1/ 1 | 0/10 | minimal bruising | mild swelling 24 hours | n/a | 15 |

TABLE 2

Lipoma Treatments:

| Patient | Site | Pre-tx meas. (cm × cm)/ area (cm²) | Post-tx meas. (cm × cm)/ area (cm²) | % Change | Number of txs/ Injection volume (mL) | Immediate Pain (1-10) | Surface change, redness (anytime) | Other Post-tx side effects | Interval Between txs (wks) | Interval between last tx and final meas. (wks) |
|---|---|---|---|---|---|---|---|---|---|---|
| 2 | Right forearm (inferior)* | 1 × 1.5/ 1.5 | 1.1 × 1.0/ 1.1 | −27 | 3/ 1 | 6/10 (<30 secs) first tx only then 0/10 | none | mild swelling 3 wks | 4 | 20 |
| 2 | Right elbow* | 1.5 × 1.5/ 2.25 | 1.2 × 1.2/ 1.44 | −36 | 3/ 1 | 6/10 (<30 secs) first tx only then 0/10 | none | mild swelling 3 wks | 4 | 20 |
| 3 | Right abdomen | 3.5 × 2.2/ 7.7 | 2 × 1.5/ 3 | −61 | 1/ 1 | 0/10 | none | none | 6 | 6 |
| 4 | Right upper back* | 4 × 2/ 8 | 2 × 2/ 4 | −50 | 2/3,2 | 0/10 all tx | none | none | 5 | 5 |
| 5 | Right forearm* | 1.5 × 1.5/ 2.25 | 1 × 1.5/ 1.5 | −33 | 3/1 | 2/10 mild burn for 1 min | none | firm × 3 wks after 1st tx | 4 | 11 |
| 5 | Right gluteal | 3.5 × 3/ 10.5 | 2 × 1.5/ 3 | −71 | 3/3, 3, 1.5 | 0/10 all tx | moderate bruising × several days | firm × 3 wks after 1st tx | 5 | 10 |
| 5 | Right upper thigh | 2 × 1.5/ 3 | 1.5 × 1/ 1.5 | −50 | 3/1.75 | 0/10 all tx | moderate bruising × several days | firm × 3 wks after 1st tx | 5 | 10 |
| 5 | Right abdomen | 2.8 × 1.5/ 4.2 | 2 × 1/ 2 | −52 | 3/1.5 | 0/10 all tx | none | firm × 3 wks after 1st tx | 5 | 10 |
| 6 | Left shoulder* | 5.5 × 4.5/ 24.8 | 3.5 × 5/ 17.5 | −29 | 2/5, 7.5 | 1/10 burn <30 secs first tx | none | mild swelling 3 days | 2, 4 | 3 |
| 6 | Right upper back | 2 × 2/ 4 | 2 × 1.75/ 3.5 | −13 | 2/2, 2 | 0/10 pinprick only | | mild swelling several days | 2, 4 | 3 | meas. = measurements
tx = treatment

TABLE 3

Utrasound Data:

| Patient | Site | Pre-tx (cm × cm × cm)/ Volume (cm$^3$) | Post-tx (cm$^3$)/ Volume (cm$^3$) | % Change | Number of tx | Interval Between txs (wks) | Interval between last tx and final meas. (wks) |
|---|---|---|---|---|---|---|---|
| 2 | Right elbow | 1.8 × 0.4 × 1.8/ 1.3 | 1.6 × 0.5 × 1.1 0.9 | −30 | 3 | 4 | 11 |
| 2 | Right forearm (inferior) | 2.1 × 0.9 × 1.8/3.4 | 1.4 × 0.6 × 1.4/ 1.2 | −64 | 3 | 4 | 11 |
| 5 | Right forearm | 2 × 2 × 2/8 | 2.6 × 1.2 × 0.3/ 0.9 | −89 | 3 | 5 | 21 |
| 4 | Right upper back | 4 × 2.3 × 0.9/ 8.3 | 2.1 × 1.7 × 0.9/ 3.2 | −62 | 2 | 5 | 4 |

Example 4: Lipoma Treatment Using 20% (v/v) Ethanol

Several patients presenting lipomas are given a preliminary examination. In general, the lipomas are discrete, mobile, non-tender subcutaneous nodules or benign tumors, and none of the patients had undergone any treatment or procedure with regard to the lipoma. Several lipomas are confirmed by ultrasound, and all lipomas are confirmed by physical examination. Each lipoma to be treated is measured using a ruler and photographed, then the skin above the lipoma is cleansed with an isopropyl alcohol swab. Repeated injections into the lipoma are spaced 1 cm apart. All injections are made directly into the lipoma. For smaller lipomas (<2 cm in diameter), the lipoma is pinched and elevated (using thumb and forefinger) prior to injection. For larger lipomas (>2 cm in diameter), injection is done directly without pinching. Depending on lipoma size, 2 mL to 8 mL of 20% ethanol is injected during one session of treatment. Treatment sessions are spaced at least 2 weeks apart.

Immediate Outcomes (Physician Examination):

Within seconds or minutes following completion of a treatment session, the area where the injections are given is examined by the physician. All patients reported minimal to no tenderness, burning or pain. In several patients, surface (skin) numbness is reported. Minimal to no skin redness is observed in any patient. Minimal to no edema (swelling) is observed in most patients. In patients injected with higher volumes of 20% ethanol (>4 mL), some edema is observed, and is judged to be proportional to the fluid volume injected and not related to an inflammatory response to the treatment.

Short Term Outcomes (within Several Days of Treatment, Patient Reported):

Patients report minimal to no tenderness 1-5 days after treatment. In those patients showing edema immediately following the treatment session, the swelling is resolved within 1-2 days. Minimal to no bruising is reported by all patients; in those patients with minimal bruising, it is transient and resolves within several days. No blisters, ulceration or numbness are reported.

Short Term Outcomes (within Several Days of Treatment, Physician Examination):

Patients are examined 1-5 days after treatment by the treating physician. Minimal redness is observed. Swelling is minimal and proportionate to the injected volume only. No skin surface changes, no ulceration, and no blistering is observed in any patient. Minimal to no bruising is observed.

Longer Term Outcomes (2 Weeks or Longer after Treatment, Physician Examination):

Patients are examined 2-4 weeks after treatment by the treating physician. Each lipoma treated is measured using a ruler and photographed. No swelling, redness, ulceration, bruising, or other changes to the skin above the lipoma is observed. Shrinkage is observed in a majority of the lipomas treated (see Table 4). The treated lipomas are observed have physical characteristics consistent with the original presentation, being discrete, mobile and non-tender.

TABLE 4

| Patient | Follow up time | Reduction in lipoma volume |
|---|---|---|
| 8 | 4 weeks | 10-30% |
| 9 | 4 weeks | 20-50% |
| 10 | 4 weeks | 40-60% |
| 11 | 4 weeks | 50-70% |
| 12 | 4 weeks | 60-80% |
| 13 | 4 weeks | 70-90% |
| 14 | 4 weeks | 80-100% |

Example 5. Lipoma Treatment Using 5% (v/v) Ethanol and 1% Polidocanol as Compared to Using 5% (v/v) Propylene Glycol and 1% Polidocanol Four patients presenting lipomas on each arm of about the same size were treated with 5% (v/v) propylene glycol and 1% polidocanol ("PG/PD") on the right arm and 0.5 cc (0.5 mL) of 5% ethanol/1% polidocanol (in water, pH adjusted to 6.5-8 using phosphate buffer, "Et/PD") on the left arm. Each lipoma to be treated is measured using a ruler and photographed, then the skin above the lipoma is cleansed with an isopropyl alcohol swab. Repeated injections into the lipoma are spaced 1 cm apart. All injections are made directly into the lipoma. The same number of injections are made in each arm. A second set of identical injections was made two weeks later.

At 1-5 days after treatment, for all four patients, the left arm, which will have been treated by Et/PD, will have less redness and swelling, as compared to the right arm, which will have been treated by PG/PD.

At four weeks, the reduction in the volume of the lipoma on the left arm, which will have been treated by Et/PD, will be 10-30% greater in the first patient, 30-60% greater in the second patient, 60-90% greater in the third patient, and 0-10% greater in the fourth patient, as compared to the reduction in the volume of the lipoma in the right arm, which will have been treated by PG/PD.

Example 6. Lipoma Treatment Using 5% (v/v) Ethanol and 1% Polidocanol as Compared to Kybella®

Four patients presenting lipomas on each arm of about the same size were treated with Kybella® on the right arm and 0.5 cc (0.5 mL) of 5% ethanol/1% polidocanol (in water, pH adjusted to 6.5-8 using phosphate buffer, "Et/PD") on the left arm. Each lipoma to be treated is measured using a ruler and photographed, then the skin above the lipoma is cleansed with an isopropyl alcohol swab. Repeated injections into the lipoma are spaced 1 cm apart. All injections are made directly into the lipoma. The same number of injections are made in each arm. A second set of identical injections was made two weeks later.

At 1-5 days after treatment, for all four patients, the left arm, which will have been treated by Et/PD, will have less redness and swelling, as compared to the right arm, which will have been treated by Kybella®.

At four weeks, the reduction in the volume of the lipoma on the left arm, which will have been treated by Et/PD, will be 10-30% greater in the first patient, 30-60% greater in the second patient, 60-90% greater in the third patient, and 0-10% greater in the fourth patient, as compared to the reduction in the volume of the lipoma in the right arm, which will have been treated by Kybella®.

Figure 11A:
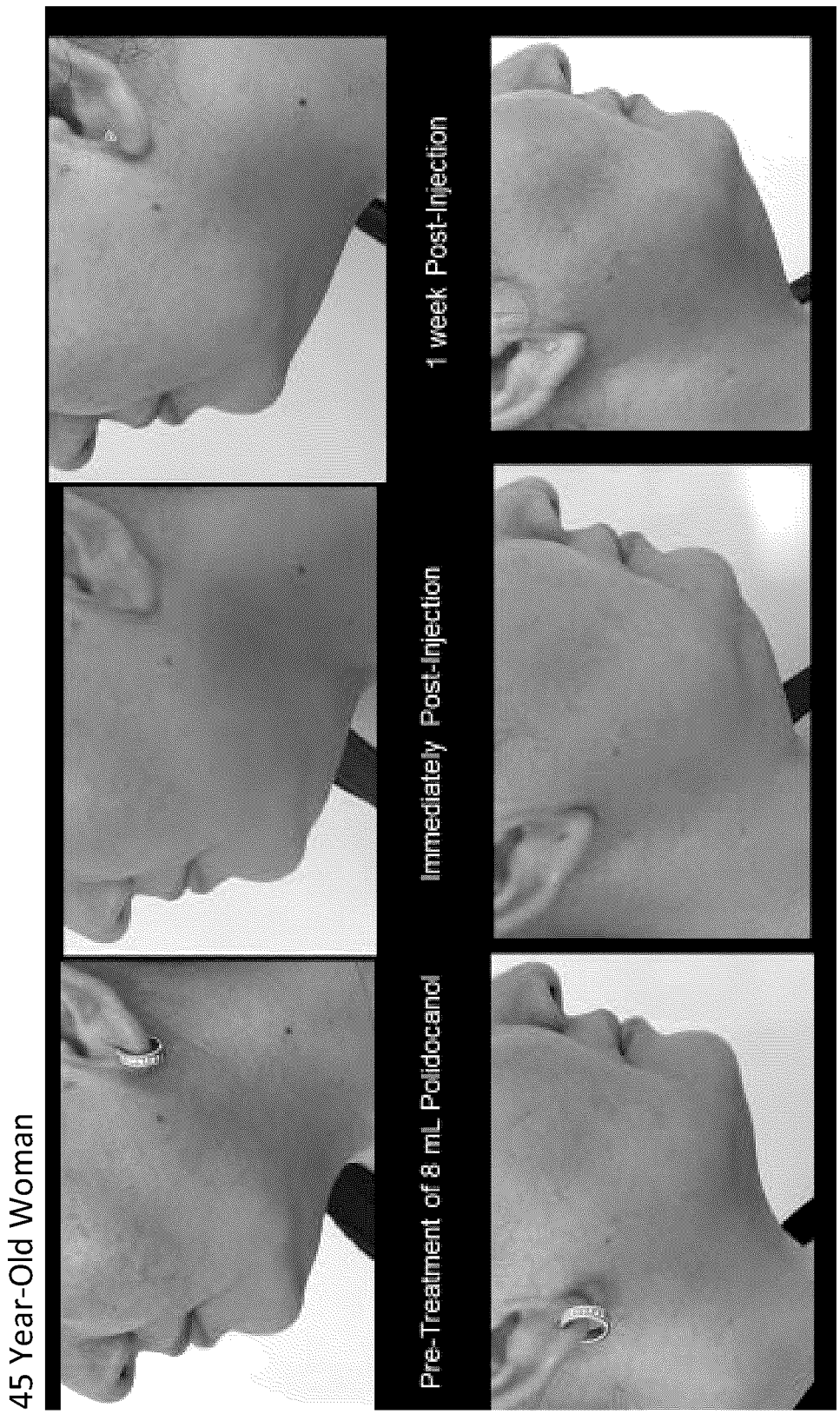
FIGS. 11A and 11B are photographs of the injection site of the patient of Example 8 before injection, 24 hours after injections, and 1 week after injections.
Figure 11B:

Example 7-Submental/Under the Chin Injection Using 5% (v/v) Ethanol and 1% Polidocanol A 5% (v/v) ethanol and 1% polidocanol solution is injected into the submental/under the chin fat of a 53 year-old woman. Injections are made 1 cm apart. FIGS. 11A and 11B are photographs of the injection site before injection and 24 hours after injections.

Figure 12A:
FIGS. 12A and 12B are photographs of the injection site of the patient of Example 9 before injection and 24 hours after injections.
Figure 12B:

Example 8-Submental/Under the Chin Injection Using 5% (v/v) Ethanol and 1% Polidocanol A 5% (v/v) ethanol and 1% polidocanol solution is injected into the submental/under the chin fat of a 45 year-old woman. Injections are made 1 cm apart. FIGS. 12A and 12B are photographs of the injection site before injection and 24 hours after injections.

Example 9-Submental/Under the Chin Injection Using 5% (v/v) Ethanol and 1% Polidocanol A 5% (v/v) ethanol and 1% polidocanol solution is injected into the submental/under the chin fat of a 25 year-old woman. Injections are made 1 cm apart. FIGS. 13A and 13B are photographs of the injection site before injection and 24 hours after injections.

What is claimed is:

1. A method of reducing fat comprising subcutaneously injecting a pharmaceutical composition into a fat deposit of an animal or a human being, wherein the pharmaceutical composition comprises ethanol and polidocanol, wherein the method is effective in reducing the weight or volume of the fat deposit.

2. The method of claim 1, further comprising a steroid.

3. The method of claim 1, further comprising a bile salt.

4. The method of claim 1, further comprising a detergent.

5. The method of claim 1, further comprising a dermal filler.

6. The method of claim 1, further comprising a neurotoxin.

7. The method of claim 1, wherein the fat deposit is a lipoma.

8. The method of claim 1, wherein the fat deposit is cellulite.

9. The method of claim 1, wherein the fat deposit is on a head.

10. The method of claim 1, wherein the fat deposit is on a neck.

11. The method of claim 1, wherein the fat deposit is on a torso.

12. The method of claim 1, wherein the fat deposit is on a buttock.

13. The method of claim 1, wherein the fat deposit is on a leg or a foot.

14. The method of claim 1, wherein the fat deposit is on an arm or a hand.

15. The method of claim 1, wherein on a single day, about 1 mg to about 20 mg of the pharmaceutical composition, per $cm^3$ of fat deposit, is injected into the fat deposit.

16. The method of claim 1, wherein the animal is a dog.

17. The method of claim 1, wherein the animal is a cat.

18. The method of claim 1, wherein the animal is a horse.

19. The method of claim 1, wherein the animal is a rabbit.

20. The method of claim 1, wherein the animal is a hamster or a Guinea pig.

* * * * *